(12) United States Patent
Postrel

(10) Patent No.: US 12,031,935 B2
(45) Date of Patent: Jul. 9, 2024

(54) INSTANT EARLY STAGE DISEASE DETECTION BY DECODING ORGANIC COMPOUND SIGNATURES

(71) Applicant: Richard Postrel, Miami Beach, FL (US)

(72) Inventor: Richard Postrel, Miami Beach, FL (US)

(*) Notice: Subject to any disclaimer, the term of this patent is extended or adjusted under 35 U.S.C. 154(b) by 500 days.

(21) Appl. No.: 17/244,140

(22) Filed: Apr. 29, 2021

(65) Prior Publication Data

US 2022/0050074 A1  Feb. 17, 2022

Related U.S. Application Data

(60) Provisional application No. 63/017,693, filed on Apr. 30, 2020.

(51) Int. Cl.
  *G01N 27/327* (2006.01)
  *G01N 27/414* (2006.01)
  *G01N 35/00* (2006.01)

(52) U.S. Cl.
  CPC ..... *G01N 27/3278* (2013.01); *G01N 27/4146* (2013.01); *G01N 35/00594* (2013.01); *G01N 2035/00306* (2013.01); *G01N 2035/00346* (2013.01)

(58) Field of Classification Search
  None
  See application file for complete search history.

(56) References Cited

U.S. PATENT DOCUMENTS

| | | | |
|---|---|---|---|
| 2006/0173580 A1* | 8/2006 | Desrochers | G01N 33/0034 73/31.01 |
| 2011/0043038 A1* | 2/2011 | Tsutsumi | H01M 10/613 429/218.2 |
| 2018/0059006 A1* | 3/2018 | Fritchie | G01N 21/27 |
| 2018/0120278 A1* | 5/2018 | Hoorfar | G01N 33/0031 |
| 2019/0000341 A1* | 1/2019 | Xu | A61B 5/6833 |
| 2019/0195809 A1* | 6/2019 | Agarwal | G01N 21/9036 |
| 2019/0383687 A1* | 12/2019 | Burssens | G01L 19/0092 |
| 2020/0086325 A1* | 3/2020 | Chou | B01L 7/52 |
| 2020/0088703 A1* | 3/2020 | Motayed | G01N 33/0031 |

* cited by examiner

*Primary Examiner* — J. Christopher Ball
*Assistant Examiner* — John C Ball

(57) ABSTRACT

The present invention provides a process and method for the early detection and diagnosis of disease by reading and decoding volatile organic compounds (VOCs) for signatures associated with a specific disease. From its outset, each disease begins producing its own unique set of volatile organic compounds. For many diseases, this early-stage detection may be many months or years before noticeable symptoms. The VOC emissions when analyzed, result in a "signature" that identifies and distinguishes the developing, or at later stages, the developed disease. The device assays non-invasively obtained biosamples in real-time to output a VOC based signature that, when correlated with data in a disease signature library, identifies one or more diseases associated with the sample.

6 Claims, 10 Drawing Sheets

INSTANT EARLY STAGE DISEASE DETECTION BY DECODING ORGANIC COMPOUND SIGNATURES

The present invention provides a process and method for the early detection and diagnosis of disease by reading and decoding volatile organic compounds (VOCs) for signatures associated with a specific disease. From its outset, each disease begins producing its own unique set of volatile organic compounds. For many diseases, this early-stage detection may be many months or years before noticeable symptoms. The VOC emissions when analyzed, result in a "signature" that identifies and distinguishes the developing, or at later stages, the developed disease. The device assays non-invasively obtained biosamples in real-time to output a VOC based signature that, when correlated with data in a disease signature library, identifies one or more diseases associated with the sample.

The invention further provides a device that optimizes the capture, classification and pattern recognition necessary for identifying a unique VOC signature from that biosample. This invention enables signature recognition for the presence of a disease at the earliest onset point of that disease. The invention disclosed herein improves patient experience and outcomes, reduces the number and extent of invasive medical procedures and reduces medical treatment costs through the early identification and detection of disease. In general, this invention increases both survivability and quality of life of patients.

BACKGROUND

Historical Introduction

Diagnosis of many diseases can be expedited with availability of easily obtainable biosamples analyzed in a rapid turnaround assay device. One category of analyses concentrates on biomolecules produced by a living organism and/or a pathogen attacking the organism. In complex animals with immune systems, diagnosis is aided by conventional assays, such as blood tests, that might provide results including, but not limited to: counts relating to numbers and types of cells in the blood, sugar(s), electrolytes, proteins/peptides of interest—including peptides complexed with carbohydrates or lipids, specific DNA or RNA fragments, etc. The present invention expands this existing library of analyses through rapid assay of volatile organic compounds (VOCs) and at a higher level comparing the outputted signature information to a VOC signature library. Signatures can be analyzed independently, averaged, and/or in combination to suggest disease status and to thereby recognize a disease signature at the onset of the disease with maximum sensitivity and selectivity. By measuring signal amplitudes of the VOCs, the present device and methods can provide a mathematical value and gauge the status of a disease and allow a practitioner to assess the progress and efficacy of a particular treatment or treatments allowing for best practice to be significantly improved.

Such signature comparisons may be useful in monitoring efficacy or progress of a chosen treatment, may assist in identifying a pathogenic disease, may monitor waxing or waning of physical condition like cancer or those relating to emotions, aging, depression, cognition, etc. A compact device as provided in accordance with the present invention capable of rapidly assaying easy to obtain non-invasive biosample material and outputting rapidly obtained analysis to determine a particular patient's biosample. As a library of VOC signatures for identifying various diseases and disease types would be a useful addition to fields of medical and/or social well-being and a defense against pathogenic disease and bioterrorism. VOC analysis in the device of the present invention may also be used to measure exposure to harmful chemicals and determine practices of avoidance or treatment, if necessary.

Historical Support

The present invention provides a device that assays products of metabolic activity with specificity sufficient to indicate and identify abnormal, e.g., unhealthy chemical reactions. The abnormal metabolic reactions may be a general indication of declining or poor health or may be more specific, i.e., indicative of a class of diseases or a specific disease. A principle feature of this invention is the ability to rapidly obtain and apply data from the assay of gaseous components that off-gas from a biologic sample to determine the presence of a disease. Several common off-gases have historically been recognized as indicators of disease and the present invention builds upon this ancient knowledge.

"Vapors" or odors have long been recognized as useful indicators of disease. For example, the ketosis exemplary of diabetes is recognized in early writings over three thousand years old. Egyptian manuscripts from around 1550 BC recognize diabetic ketosis and sweet urine. Sweet urine and ketone breath along with polyuria were recognized as a signal of an impending death. Unani physicians today rely chiefly on urine, especially its smells, to aid disease diagnosis.

Today we know the underlying chemical and biological bases for diabetes and many other diseases. Multiple diseases have been associated with one or more of various organic compounds. In the $20^{th}$ and $21^{st}$ centuries, increased sensitivity of electronic chemical detectors, often called "electronic noses" has allowed the use of "vapors" or odors to confirm or correlate with diagnoses for diseases including, but not limited to: prostate cancer, breast cancers, renal disease, diabetes, etc.

For example, Tanzeela Khalid, et al., in "Urinary Volatile Organic Compounds for the Detection of Prostate Cancer" published an article whose aim was to investigate volatile organic compounds (VOCs) emanating from urine samples to determine whether they can be used to classify samples into those from prostate cancer and non-cancer groups. They used mass spectrometry (MS) coupled with gas chromatography (GC) to analyze the headspace over collected urine as a sample source and thereby determined that using four volatile organic compounds (VOCs) in the detection regimen improved the accuracy of prostate detection over that of PSA alone. Similarly, in another study, urine was analyzed for content of over 60 VOCs to correlate patterns associated with breast cancers.

Urine is an excellent source for sampling, as the renal system filters and concentrates compounds from the blood coursing through the kidneys. Thus, information from the entire body is stored in urine. Breath can also be used, as well as plasma, saliva, sweat, semen, mucous, lymph, feces, and extracts or lysed cells such as blood cells or cells obtained in biopsy of any organ, including, but not limited to: skin, liver, lung kidney, muscle, etc. If gas, like breath, axillary odors or fumes, gases emitted from foot or hand or other body zone or part is sampled, the gas itself is considered as a sample off-gas. Breath, a product of the GI and pulmonary systems, has a lower variety of VOCs, has higher levels of contaminating VOCs from the environment and includes significant quantities of VOCs produced by the microbiomes residing in and on the organism, rather than the actual cells of the organism making high degree of specificity more difficult to achieve, in particular at the onset of a disease in the organism. In practice, the invention can assay VOCs from gas or off-gas from any source of interest, including biological sources including, but not limited to: urine, blood, tears, sweat, plasma, flatulence, lymph, semen, vagina secretions, feces, wounds and/or festering wounds, breath, saliva, gas (VOC) emissions from a collection of animals or people, an individual, any internal or external surfaces (including the hand, armpits, scalp, sinuses, ear canal, ear folds, feet, navel, esophageal gas, vaginal gas, urethral gas, or umbilicus), etc. An internal probe may be used to sample mucus or liquids and/or to sample gases from the regions.

Advanced Analytics

The process of decoding the VOC emissions to arrive at disease profiles and signatures starts with a sample or samples being fed into the sensing device. A sample may be isolated or collected from the intended source and gases emitted therefrom fed into the device. A liquid sample may be fed into the device where off-gassing delivers the VOCs into a sensor chamber or zone. A simple wave of the hand near or over the sensing compartment may feed the sample into the device for analysis. A probe, or powered inhaler, such as a straw, tube, wand, or rod may collect gases from a targeted location. Gaseous samples collected remotely or at the device initiate the analytical decoding process.

The gas contacts a "chip" carrying multiple sensing elements. The sensing elements on the chip change their outputs when a VOC molecule approaches and interacts with the sensor surface. A bio-molecular detection cartridge serves as the gateway to disease signature production. The detection cartridge incorporates the chip with circuitry that collects and outputs the sensor signal data. Analysis may take place in real time or the data may be stored. The bio-molecular detection cartridge may be incorporated in a free-standing testing unit that collects analyzes, produces a signature or profile, compares this to a database of signatures and reports matches. Any stage of the process following collection of sensor data may be performed remotely. The device may transmit its results to a consolidator that may be on-site or acting as a distant service, e.g., the cloud or a similar central data storage and processing facility.

A cartridge may produce its own output in accordance with its design, e.g., a sound, a light, a visual display, opening or closing a barricade, a report transmitted though hard connection, e.g., fiber optic or electric contact, electromagnetic radiation, etc. The electromagnetic radiation may include a light signal, e.g., infrared, visible or ultraviolet light, a cellular or WiFi communication system, a portal that the cartridge may rest upon for inductive transfer, etc. When operating in conjunction with, but not physically incorporated in a package with the reporting unit, the bio-molecular detection cartridge may transmit data by any desired communication means. Data may be transmitted as discussed above, but requiring greater power when greater distances are involved. Intermediate communication devices may be used in combination with other components. For example, an antenna may transmit to a WiFi router that may interface though an Ethernet cable to a server. The server may produce a report or may transmit its data to a cloud server for final processing and data storage. An output report may be saved until queried or may be transmitted to requesting or assigned parties. A cartridge may continuously collect data or may be activated by a command or by sensors associated with the cartridge. Output may be continuous transmitted or transmitted in accordance with a time schedule, a detection signal indicating a hazard, a data content threshold being reached or exceeded, or any other chosen trigger. A cartridge may collect and store data until connected to a data analyzer or an interface to a remote component. One contemporary illustration would have a small, possibly pocket sized, bio-molecular detection cartridge use a USB port for a hardwired connection.

VOCs in the sample gas interact with sensors on the chip. As a VOC passes by or over a sensing element, the electron cloud of one or more parts of the VOC alters the electron cloud on the sensing element. The interaction may drive rotation of the VOC causing additional cloud adaptations. Each shift of the sensing element electron cloud is recorded for pattern recognition analysis. An analogue to digital conversion, using one of the commercially available devices provides adequate results. Devices are available across a range of prices bit depth and sampling rates. Devices or chips presenting with a bit depth of 20 (resolution >1M), 24 (resolution >16M), 28 (resolution >250M), 32 (resolution >4B), are generally available. Sampling rates ranging from 5 kHz to 96 kHZ are competitively marketed. Samplings taken every 50 μsec (20 kHz) prove more than adequate for producing disease distinguishing signatures. Major chip suppliers include but are not limited to: Analog Devices, Inc.; Microchip Technology Inc.; Sony Corporation; Maxim Integrated; Adafruit Industries; Texas Instruments Incorporated; Asahi Kasei Microdevices Co.; Renesas Electronics Corporation; National Instruments; Diligent Inc.; etc. The digital output is processed, e.g., using linear discriminant analysis (LDA), normal discriminant analysis (NDA), or discriminant function analysis (DFA).

Numerous sensors will simultaneously be reporting their electronic activities. A plurality of sensing element characteristics will increase the differentiation capacity of the device. For example, a plurality of decorations, 4, 8, 10, 12, 16, 24, 32 being arbitrary examples, may be disposed across multiple sensors. A plurality of each type decoration will reduce randomness of the VOC interactions with that type of sensing element. VOC discrimination or differentiation capacity may be further increased by other means, such as running sensing elements at two, three, four, or more different temperatures. Base or feeder voltage can also be used as an additional tool for increasing discrimination by contributing a variety of field strengths affecting VOC movement and orientation. A selective filter, e.g., by size (perforation or pore), chemical, photo-attraction or repulsion, may also be used to improve differentiation and discrimination.

A rudimentary chip may support 100 sensing elements, perhaps in a 10×10 square. Maybe 10 decorations are distributed equally across the chip in a pseudo random pattern. Other formats may involve, e.g., an 8×16 endowed chip, a 12×12, 16×16, 16×32, 32×32, 32×64, 64×64, etc., pattern on a chip. These specific architectures are arbitrary depictions. These examples were chosen as illustrations, since in computer analysis, binary (multipliers or powers or 2) formats are common in the computer hardware. Powers of ten or another base may be appropriate for selected useful patternings.

Greater numbers of sensing elements on a chip provides opportunity for greater differentiation capacities. The greater differentiation should allow a greater population of the VOCs to provide meaningful information and to be incorporate into the signatures.

When a specific detection task is at hand, and several of the types of decorations, voltages, temperatures, or other differentiating mechanism are known not contribute to the signature outcome, these may be ignored in the analysis or may be turned off to simplify data processing. A physical mask may be used to block VOCs from interacting with a group or groups of sensing elements. The decoding process will assign weightings to each of the contributing sensing element groups to maximize detection and discrimination outcomes.

The sample having been fed into the device, the sensing element electron clouds are recorded. The patterns of the interactions of various sensors with the VOCs are recorded. Pattern recognition is used to categorize the interactions associated with a particular disease or condition in a particular set of circumstances. Analyses from several individuals with the same disease or condition will allow the random (not disease associated) VOC patterns to be set aside. Control individuals, i.e., those without the disease or condition, will provide a subtraction sample to guide the pattern recognition processes to ignore the irrelevant VOCs. The interactions involving relevant VOCs are then scored for their contribution to the discrimination abilities of the suggested diagnoses. Multi-dimensional regression analysis has proven useful in such determinations, though other statistics proven in conventional artificial intelligence, pattern recognition practices may be applied here.

To date laborious techniques such as MS/GC have been the preferred analytical tool for VOC analysis. Improvements in detection sensitivity from micro-detection to nano-detection using highly advanced sensors now enables a more robust use of nano-analysis of VOCs and other compounds and when combined with rapid data analysis and machine learning can: a) confirm a diagnosis, b) assist in selecting or ranking diagnoses and/or c) suggest one or more diagnoses even prior to outward symptoms becoming apparent. After assay, in some circumstances simply questioning a patient about a result may elucidate an overlooked symptom of disease.

The system/device may be fine-tuned. For example, a device comprising $2^{12}$ sensing elements may include $2^5$ different decorations on the carbon sensing bases. Assuming equal numbers of each which is not necessarily a valid assumption since one or more functionalizing compounds may be favored for disposition in multiples, e.g., 2, 3, 4, 5, $2^3$, $10^1$, $2^4$, $2^5$, $2^6$, $2^7$, $2^8$, $2^9$, $2^{10}$, $10^2$, $2^{11}$, $2^{12}$, etc., of those less favored. Modulating factors, e.g., temperature, thickness, density of decorations, mix of decorations, height off base, voltage, thickness, etc., may differentiate sensor characteristics. Multiple copies of each sensor characteristic class are preferred to increase repeatability of results. An increased number of sensor element characteristics will increase the population of VOCs, that are discriminated in any one run. The multiplicity of sensor characteristics permits an operator or algorithm to select a subpopulation of sensors for data analysis during an individual assessment to concentrate on a desired disease/condition or demographic profile.

The general approach of monitoring VOCs for detecting disease has been in development for several decades and now is soundly acknowledged in developing science and health medicine. In accord with the present invention a device to achieve these VOC assay goals has been designed to assay a variety of volatile organic compounds (VOCs) in a rapid and reproducible fashion. Under the present invention, multiple disease signatures can now be searched from the same sample simultaneously. The basic benefits of measuring VOCs for disease detection have been recognized in medicine for quite some time. In a 2014 Clinical Policy Bulletin, Aetna explained its policy regarding VOC analysis at that time as:

Aetna considers the analysis of volatile organic compounds experimental and investigational for the following indications (not an all-inclusive list) because the clinical effectiveness of this technique has not been established:

Detection of bacteriuria
Detection of cancer (e.g., breast cancer, colorectal cancer, lung cancer and cancer of the pleura, pancreatic cancer; not an all-inclusive list)
Diagnosis of amyotrophic lateral sclerosis
Diagnosis of autism spectrum disorders
Diagnosis of inflammatory bowel disease
Diagnosis of juvenile idiopathic arthritis
Diagnosis of non-alcoholic fatty liver disease
Differential diagnosis of breast diseases (e.g., breast cancer, cyclomastopathy, and mammary gland fibroma)
Prediction of development of childhood obesity
Use as markers for monitoring hemodialysis efficiency[1]

[1] Clinical Policy Bulletin: Analysis of Volatile Organic Compounds. Number: 0717. Revised April 2014. Obtained from: http://qawww.aetna.com/cpb/medical/data/700_799/0717_draft.html Advances in VOC Technology Urine, exhaled breath and blood are recognized as available sample sources. The present invention may use these and/or samples including, but not limited to: saliva, perspiration, fecal material, skin (or other organ biopsy) as a source for the assay.

A device, as described herein, capable of providing signature information from a variety of assays, including bioassays or assays of structures suspected of emitting possible harmful compounds into ambient atmosphere meets multiple identified needs and applications.

The device of the present invention provides rapid highly sensitive detection of VOCs in a gas phase sample. Analytical data are then processed using the device's library of algorithms to detect a disease or to answer questions for which the sample was taken. Through machine learning and artificial intelligence, the device is continually developing and improving its algorithms. A disease that has newly adapted to infect the human population may be identified by type, e.g., a family, genus, zoonotic source, etc., before the disease is formally recognized. The scope of infection becomes apparent with each sample associated with the previously unencountered signature. A new disease may be detected as a variant with a mere handful of samples that produce signatures similar to, but differentiated from, a known disease. Spread of the variant can then be monitored. A new disease profile or draft signature may be correlated with a set of symptoms and a previously unencountered set of VOCs.

The method may involve multiple layers of machine learning. A starter cohort of persons, perhaps a score or fewer, with and without a condition or disease of interest may be sampled to form a "rapid" profile of discriminatory VOC patterns. These patterns will be distinguished as condition/disease positive and condition/disease negative. A high specificity will be used to select the VOCs and their characteristics to form this primitive signature. GC/MS and/or other analytical methods may be used to determine structure of the VOCs in this primitive profile signature. The device may then be used with patient consent to obtain larger sample sizes. Preferably primitive profiles are determined for a plurality of diseases/conditions allowing positives for one or more disease/conditions to serve as negatives for others. as the cohorts grow in size additional results will be incorporated into the algorithm to fine tune sensitivity.

As the groups providing samples become more diverse sufficient data becomes available to further improve specificity and sensitivity with respect to gender, race, age, occupational hazard, region, and/or genetic information available for an individual. The developing universal cohort data set is used when demographic information is unavailable or is protected by patient choice, law, regulation, policy, etc. Where demographics are available a second or other version relevant to the demographic group(s) will be used for assessment. A report may include both a universal and a demographically weighted assessment. Such assessments preferably will include a probability of the correctness of each suggested disease/condition. As the data sets mature, a single VOC assessment may be obtained for each patient entering a practice or facility for treatment. Such general screenings will detect diseases/conditions unknown to the patient and possibly in development and not apparent from symptom analysis. An individual's results may be scored with a rating, e.g., a percentage or other weighting relating to a clinician's self entered or experiencially derived probability that the diagnosis for a disease/condition is true. As use of the device becomes more conventional, the device may be used as a background screen. For example, a patient with a pain or inflammation, e.g., sinusitis, pancreatitis, hepatitis, etc., may be screened with the symptom entered into the system. A subsequent diagnosis, e.g., hepatitis C, hepatic cancer, pancreatic cancer, etc., may be associated with the disease pathway and used for clinical advisement.

One specific application of the preset invention is natal screening. Fumes from the baby or the afterbirth may be analyzed and decoded as part of the preliminary screening, especially for multiple potential genetic diseases. A single liquid or gas sample may be rapidly, almost instantly, analyzed for multiple conditions. This provides more rapid results at a marginal cost well below PCR, ELISA, or other conventional screening tools.

Through capturing the VOCs in vapor or gas phase to measure the presence, amounts, volume, intensity or strength of signal of multiple VOCs, then classifying each signal as from the organism or the environment and removing foreign VOCs from analysis consideration, the device then outputs a sample's gross output of organism initiated organic compounds for comparison to the signature database to determine whether a specific disease (or set of diseases) is present. The present invention continues to consolidate VOC signature profiles into a library as new sample outputs are presented.

In addition, the device may physically incorporate add-on devices and/or applications, for example, a capillary analytical attachment, including, but not limited to: capillary electrophoresis, capillary chromatography, capillary ELISA, nano-sensors similar to the vapor phase sensors but proximal to analyte in a liquid phase, etc. Add-on devices may be analytical providing additional information to be used in data analysis and signature identification or in some embodiments may absorb, adsorb, catalytically modify and/or filter out potential confounding compounds and thereby minimize the necessity for applying algorithms to remove the undesired ambient VOCs. The machine learning component of the invention, in preferred embodiments, has capacity for inclusion of externally generated information from add-on devices and/or from externally provided information.

One preferred format of the present invention features "chips" with modular nano-sensing elements (or nano-sensor element (NSE) that are independently maintained at a fixed, fluctuating, stochastic, alternating, discontinuous or flashing feeder power supply. The outputs of each NSE may be individually wired to a dedicated data transducer or a selection of sensor outputs may use a common carrier circuit and thus be "averaged". In some embodiments, a simpler circuitry may involve multiple elements feeding a single output that may sum the outputs to deliver an average reading. When one or more of the "averaged" sensors is turned off or powered down, the average will not include output from these one or more powered down sensors. When input sensors are powered individually, for example, in a cycling pattern when only one (or a selected portion) of the input electrodes being charged, averaged outputs synchronized with the timing of input charging can thus provide data from individual channels.

The single output may connect and thereby collect data signal from any desired fraction of elements. For example, a single output may receive signal from all elements on a chip, half the elements on a chip, one-third the elements on a chip, a quarter the elements on a chip, a fifth the elements on a chip, and so on, for example, $\frac{1}{6}$, $\frac{1}{7}$, $\frac{1}{8}$, $\frac{1}{9}$, $\frac{1}{10}$, $\frac{1}{12}$, $\frac{1}{20}$, $\frac{1}{25}$, $\frac{1}{33}$, $\frac{1}{50}$, $\frac{1}{100}$, etc. Any output may be associated with 1, 2, 3, 4, 5, 6, 7, 8, 9, 10, 11, 12, 13, 14, 15, 16, 17, 18, 19, 20, 21, 22, . . . , 24, . . . , 32, . . . , 48, . . . , 50, . . . , 64, . . . , 96, . . . , 100, . . . , 128, . . . , 200, . . . , 250, . . . , 256, . . . , 500, . . . , 512, . . . , 1000, . . . , 1024, . . . , 2048, . . . , 4096, . . . , 5000, . . . , 8192, . . . , 10,000 ($10^4$), . . . , 16,384, . . . , $2^{15}$, . . . , $2^{16}$, . . . , $10^5$, . . . , $2^{17}$, . . . , $2^{18}$, . . . , $2^{19}$, $10^6$, . . . , $2^{20}$, . . . , total number of sensors on a chip which may vary with time or programmed instructions. The precise count of sensor elements associated with any output in general is a design feature and does not define operative functions of the invention. The counts specifically exemplified above are exemplary low numbers of sensors that may feed an output and higher numbers common in conventional plate assays and powers of 2 and 10 frequently used or approximated in biological or chemical science or physics or electronics.

When connected to multiple elements, the output averaging output signals from each, connection of each element is optionally modulated to alter weightings of elements in the average. With fluctuating or non-constant inputs weighting is also controllable. For example, in an extreme sense a stochastic or alternating input, when alternated to off that element's output will report a zero weighting, or a fluctuating or stochastic feed can serve to physically, rather than mathematically control the weighting output. The designer and/or operator will have options for mathematical/algorithmic or physical/electrical weighting of each NSE input to the data analysis. A group of elements may therefore receive the same feeder voltage, or the feeders may be independently controlled.

Instruction to or control of the system may be through information encoded on a sample package, information encoded on a sensor chip, from a user interface, information provided remotely by machine or active user, or information encoded within the device. For example, samples may be encoded with a shape or mass signal. A sample having a given shape would instruct the device to proceed with the assay that the software associates with that shape. In addition to shape, sample cartridge mass may be instructive as to the sample mass itself or may, perhaps distinguishing a smaller or a larger sample, instruct processing of the sample to allow access at controlled volume or feed rate of the VOCs into analysis. An optically readable signal, (color, transparency, bar code, text, etc.) an electronically accessible signal (RFID, memory chip or drive, etc.), a magnetic signal, etc., are also usable in controlling the device. Specific control can be through a large variety of means and is not generally to be considered as limiting the invention. The signal embedded itself may be adequate to program the relevant machine cycles or may instruct the machine to access further instructions for example, in machine archives or at a remote location. A device may cycle through one or a plurality of signals as directed or required. Chips may be interchangeable and be encoded using signals analogous to those discussed above relating to sample cartridges.

A remote location providing instruction, collection, processing, and/or storage of data may be proximal to the device, i.e., in the same building, or may be distant, e.g., an unknown location in the cloud. Instructions may be self-sufficient or may query for further input from an operator or a distant database. Remote instructions may be signaled for production and delivery, for example, when the device is actuated by turning on or introducing a sample. Instructions may be stored in an arbitrary location such as the cloud which the device queries for specific operational signals. Remote signaling may be updated in accordance with experience of sister devices which can involve a neuro-like network. The remote instructions may be of any form, for example, explicit temporal instructions relating to each controllable variable, or more simply, to instruct to initiate one or a series of protocol apps available to the machine. For security purposes the device may require identification such as an access card, access code, facial or bio-recognition, etc. to shield against unauthorized use. The device may be configured in many formats, e.g., as a portable point of care device, a mobile high throughput application, a fixed regional installation for massive scalable testing, etc.

Organization of NSEs

The sensor elements are preferably nano-sensor elements (NSEs) to minimize size and maximize sensitivity of the sensing chip. NSEs will in general be mounted or carried on a substrate or support matrix forming a "chip". Individual matrices may feature multiple elements, generally 10 or more, 32 or more, 50 or more, or larger populations of elements on a single chip. As a rule, a greater number on a chip promotes a compactness desired for minimizing weight and size. The number of NSEs is a design feature and can mimic numbers familiar to the operator or data analyst. For example, multiple of the number of wells common on petri dishes may facilitate using existing software tools to further analyze and compare results. Powers of ten, multiples of a hundred or thousand, powers of two are in common use. Accordingly, about 96 elements, 100 elements, 128 elements, 144 elements, 200 or 256 elements, 500 or 512 elements, $10^3$ or $2^{10}$ elements, $10^4$, $2^{20}$, $10^6$, etc., may be built in as common useful working populations even if several elements on the chip are not activated.

Minor variances in sensor sensitivities may be weighted internally by the machine software or may be overcome by averaging signals of a subpopulation of chips. This massaging feature is available as a tool to promote inter-device and/or inter-chip consistency.

NSEs carried on the chips can be any properly designed sensing surface capable of, for example, field-effect transistor (FET) or other physico-electrical property/activity including, but not limited to: semi-conducting nano-wires, carbon nano-tubes—including single-wall carbon nano-tubes, chitosan-cantilever based, synthetic polymers—including dendrimers, plasmon resonance nano-sensors, Förster resonance energy transfer nano-sensors, vibrational phonon nano-sensors, optical emitting, optical frequency (or wavelength) based nano-sensors (sensitive to photon transmittance, absorption, reflection, energy modulation, etc.). Nano FETs and other nano-sensor formats generally operate by changing electrical properties as a substance comes in close proximity to the sensor by perturbing the steady state (absent the proximal substance) charges and movements (distribution of electrons) within the nano-sensor. When the transistor effective electrical properties cause an observable change in electron flow (current) this manifestation is one example of sensor competence. The altered distribution of electrons, depending on the design of the nano-sensor, changes one or more electrical properties, e.g., impedance, resistance-conductivity, capacitance, inductance, etc. and thus the physical movement of a detectable particle, e.g., an electron, a photon, etc.

The discussion in this disclosure of the present invention primarily features nano-sensors whose characteristics change depending on association (close proximity with) a chemical substance. Sensation may involve more than one event. For example, in one format of nano-sensor the proximity event may dampen a vibration that is sensed by observing a changed electrical property. Similarly, an optical property, e.g., reflectance, transmittance, refractive index, can be perturbed by proximity to a substance, altering electron distribution within the sensor enough to cause optically detectable geometric changes. The optically related detection format for a nano-sensor may be observed at a specific frequency or range of frequencies, for example moving peak transmittance to another frequency.

Nano-sensors are classified in different ways, for example, the feature being assayed, e.g., movement, temperature, frequency, chemical, current, voltage, etc.; or output, e.g., fluorescence, light, electric property, etc. For example, a fluorescence outputting nano-sensor may be carbon based, e.g., single walled carbon nanotube, graphene, quantum dot based, nucleic acid (RNA, DNA), peptide based, organic polymer based, etc. Photo-acoustic, plasmonic, magnetic, etc. perturbations are also useful as bio-sensors and may be applied in features of the present invention.

Embodiments of the invention may be designed for ambient temperatures and pressures common on earth, but special designs may be configured for vacuum or high pressure, extreme cold (including biologic storage freezers, liquid He, superconducting cold environments, furnace temperatures, combustion chamber temperatures, etc.

One format extensively described as an example herein involves use of carbon-based structures having properties similar to decorated single wall nanotubules (SWNTs). The carbon component atoms of the nano-tubules are receptive to complexing with ringed chemical structures (decorations or functionalizations), often occurring through a non-covalent π-bonding effect. Graphene, having similar single layer carbon geometry, with proper decoration, can also serve as a sensing surface. Evidence indicates the curved carbon structures of the SWNTs demonstrate more consistent FET properties in many use environments with various functionalization (decoration). Therefore, curved graphene, possibly formed into a corrugated or spiral geometry, (See, e.g., Michael Taeyoung Hwang, et al., Ultrasensitive detection of nucleic acids using deformed graphene channel field effect biosensors. *Nat Commun* 11, 1543 (2020). https://doi.org/10.1038/s41467-020-15330-9) may demonstrate more promising specificity, speed of analysis, and/or sensitivity over planar graphene for particular applications. As nano-technology continues to progress additional sensor formats such as those emitting light, will become accepted in the art. Embodiments of the present invention may incorporate these improved sensors as their reliability is established. The skilled artisan will generally choose which form of sensor is optimal for performance and cost.

In addition to the field effect electrical sensing set forth as a preferred embodiment, other qualities of thin carbon based used for sensing are possible. Optical, electrochemical or electrical features have been employed with graphene-based biosensors. Forms of graphene have been successfully tested for electrochemical (amperometric, voltammetric, impedimetric, or combinations thereof) and electrical sensing applications. Selected formats have the high electron transfer rate, the high charge-carrier mobility and manageable electrical noise that is necessary for sensitive detection of biomarkers and other biological analytes. Successful assays have been reported in both serum and blood extracts. Optical transparency of graphene monolayers allows use in sensors such as optical-based G-biosensors.

The NSEs themselves or at least portions of the device surrounding the chips are preferably surrounded by a controlled gaseous atmosphere, generally slightly above ambient pressure. The sensing chamber itself may have a reduced pressure with respect to the sample introduction area. A positive device pressure at at least one level surrounding the assay chamber is generally preferred to minimize possibility of contaminating inflows. The actual pressure where sensing is accomplished however can be varied. VOCs may be delivered by having a negative relative pressure in the chip area with respect to a sample containment or introduction area to cause drawing in sample off-gas when the off-gas collection volume and the sensing volume become connected. VOCs themselves, for example, when heated may produce the pressure difference to drive delivery to the sensor volume.

Since physical delivery or movement is required to bring a candidate compound in contact with a NSE, a physical intervention is required. Physical movement can be induced as desired by any appropriate force. Forces may be constant, variable, stepped or pulsed, etc. Multiple forces may be used in series or parallel for sample delivery or a single force may be selected from the device's repertoire to enhance delivery and detection of the sample to the NSE(s).

For example, temperature can control speed and movement of target compounds and ambient gases driving the sample compounds to the sensor; pressure difference can induce a convective movement. Pressured gas canisters may provide the driving force. Other forces including, but not limited to: electric, magnetic, electromagnetic, acoustic, photo-excitation or photon momentum, etc., may be selected depending on particular circumstance. Forces may be described in a number of ways. For example, a decrease in temperature may induce a relative vacuum thereby creating a convective force. An acoustic force, for example, having one or more oscillating frequencies in a range perhaps between 10 mHz and 100 MHz will often exhibit one or more harmonics (or multiple frequencies). Echoes may result in one or more frequencies that are distinct from the feeder frequency. Geometry and chemical composition of the device may accentuate or dampen frequencies. The acoustic engineer will take into account the importance of such effects when designing the device.

The gaseous environment in the present invention is an improvement over prior applications of FET sensing in that the response is both quicker and reversible. Reversibility is critical for high-throughput commercial applications in that it allows for the rapid turnover of samples through avoidance of disassembly and/or cleaning between sample readings. The NSEs on a chip are thus available to assay hundreds or thousands of samples in a day. Reversibility can be accomplished simply by increasing the temperature. Flushing with the ambient gas or another gas can also be used. Continuing to monitor the output signaling from the NSEs provides assurance that the sample has been reversibly cleared and the device is in a mode to accept the next sample.

The gases or atmosphere surrounding the sensors will comprise molecules that interact with NSEs to—after signal generation, transduction and processing—output information relating to the components in the vapor from the sample being examined. Pressure within the testing chamber is preferably maintained by controllably providing a non-reactive or inert gas. Argon is such a gas often used in manufacture and medical applications, and helium, nitrogen, neon and xenon may also meet the needs of non-reactive or inert applications. Some applications may suggest using a mixture of gases maintained at conditions compatible with testing. For example an extremely light gas such as hydrogen or extremely dense gas such as tungsten hexafluoride may be the only gas used in certain applications or may be admixed to arrive at desired properties, including, but not limited to: acoustic, temperature, reactivity, shielding, polarization, etc. The specific gases used for assaying samples comprise one controllable variable that may be maintained as constant or varied during an individual sample reading.

At least one, but often a plurality of sensor chips, may be included in a device. During use, the sensor chips will be mounted in a controlled atmosphere chamber where vapor phase analyte will be introduced to contact with the sensor chips and thus the NSEs. During analysis, input and output voltages are provided and monitored, respectively, as analyte is delivered to the ambient volume over the chip. Only a vapor phase analyte contacts the NSEs. This provides advantages over many liquid phase SWNT and similar sensors in that sensor size can be reduced without having to account for surface tension, liquid phase excipients are not necessary and turnover rate is not compromised by the requirement to remove the liquid carrier.

Sample Suitability

For medical applications, the analyte sample is most preferably a non-invasive, readily available, biopsied sample, though in some applications a breath or ambient air sample may be collected. Urine is an excellent biopsy sample, given that urine includes filtrate from the entire body and is non-invasively obtainable. Urine is especially preferred in that it is a sterile medium with no known shedding of SARS-CoV-2 virus or particulates. Urine is also easily collected using sterile technique without any specialized training. However, in specific cases a biopsy from any tissue may be analyzed. Non-urine biopsies may involve additional preparation such as cell lysis, centrifugation, washing, extraction, etc.

A feeder cartridge is used to present the sample. The present invention is not limited to any specific feeding protocol. For example, the device may be fed manually, by a machine carousel, by a linear feed, by a high rate delivering robotic system, etc. In one preferred embodiment the cartridge in lined up in a queue for delivery to the device. The cartridge can bear identification allowing tracing of the sample through data collection, signal transduction up through final output. Several analytical processes may be chosen. The cartridge may contain or support the sample in any suitable presentation format, including, but not limited to: in a pierceable liquid container, an open top container, a container sporting an access port, a charged gas cartridge or gas cartridge with other ability for expelling a sample, a spongy material (such as a synthetic plastic or foam or a natural material such as a fiber like cotton) for presenting the sample, a dried or lyophilized sample for reconstitution, a frozen sample, a piston device (e.g., a syringe), etc. In especially elegant applications a photon momentum force can be applied in an atomic tweezer fashion. Selectivity can be further enhanced by tuning the light frequency to optimize retention or exclusion of different compound species.

BRIEF DESCRIPTION OF THE DRAWINGS

FIG. 4. A cutaway view of the device of FIG. 3 is shown. The pin connector 43 couples the nanosensing housing 44 through electronics box 32 to the pin receiver 45. The nano sensor plate 46 is shown supporting four nanosensor housing units 44 on four PC boards 30. Sixteen wells 2 are arranged in a circular pattern on a well plate 47 above the lift plate 38. To be able to correspond with well access panels 48 separated by isolation partitions 49. A lower partition 52 serves to isolate the motor 36, 39, pumps 51, batteries 50, etc., while allowing air hoses 9 to the well plate stations 2 to pass through.

In FIG. 6A, Installation of Well-Carrying Plate, a nano sensor plate 46 is shown above a nanosensor 1. Retractable panel 1 78 and retractable panel 2 79 are shown atop the well plate 47. Two wells, well 1 2a and well 2 2b are shown adjacent to one another. Well plate station 1 2a has the piston 80 retracted in FIG. 6A. The heater 71 rests on a lift block 81 atop the lift plate 38. In FIG. 6B, Well Lifted and Opens Panels, the piston 80 has lifted to elevate the lift plate 38, the lift block 81 and the heater 71 up to the well plate 47 and well 1 2a. Panel 1 78 and panel 2 79 are raised are raised to form sample sidewalls above the well plate 47. The arrows in FIG. 6B show movement with respect to FIG. 6A.

OPERATION OF THE DEVICE

Figure 1:
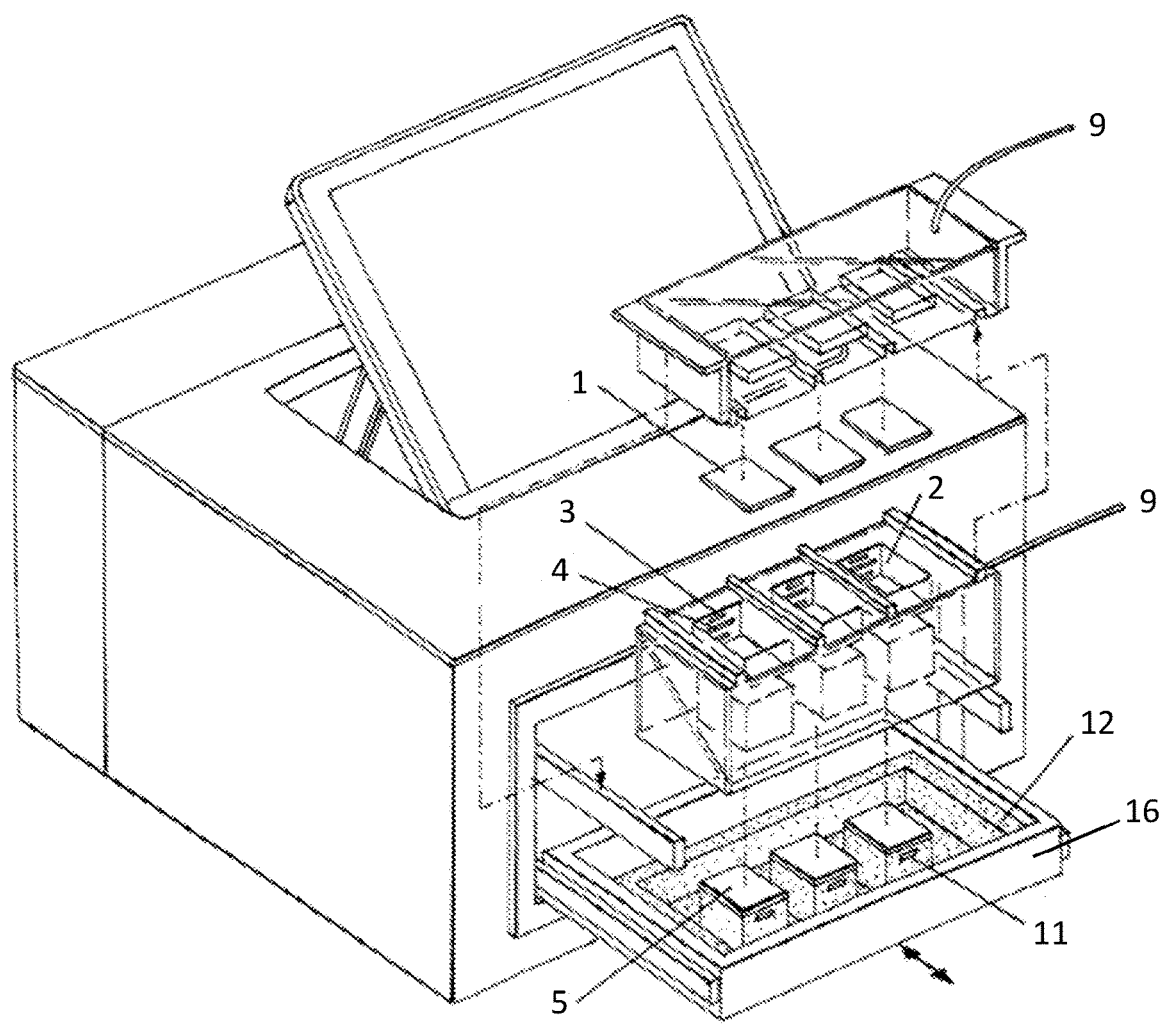
FIG. 1. Shows an apparatus with three wells 2. Nanosensors 1 are configured to enclose or ride atop the wells 2. Temperature sensors 3, pressure sensors 4, heater plates 5, under feedback control of a heat sensor 11 are supported on a nonstick coated 12 slidable plate or drawer 16. Gas ports 9 are also shown.
Figure 1:
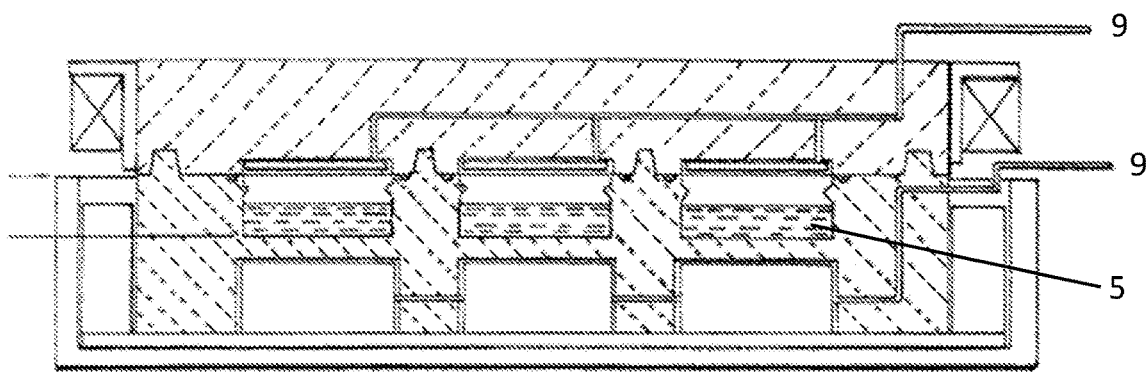
Figure 2:
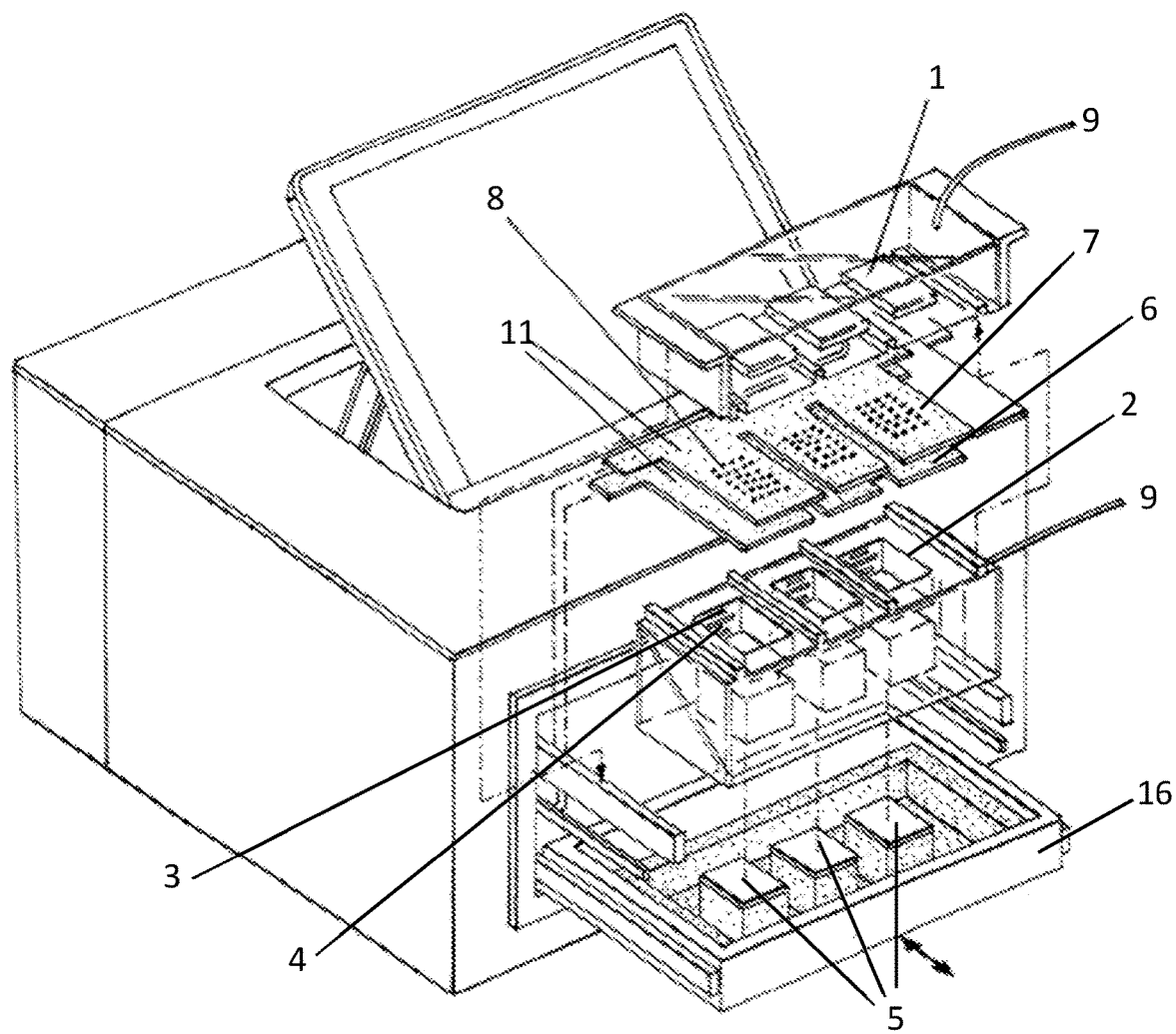
FIG. 2. A nano-sensor chip 1 is positioned at the top of a plasma well 2. The well 2 incorporates auxiliary sensors, for example, a temperature sensor 3 and/or a pressure sensor 4. A tray or drawer 16 may be removable, slidably accessible, accessible through an openable or removable port, door, cover and/or the like. Retractable and/or replaceable panels may be slidably inserted in the device to provide solid 6 or perforated 7 barricade where separation/isolation or elemental directed access is provided. The perforated slidable panel 7 may employ offsettable perforations 8 to control access allowing convective access of analyte to elements in an open position and shutting off access in a closed position. Gas ports 9 serve to deliver and/or exhaust gases.
Figure 2:
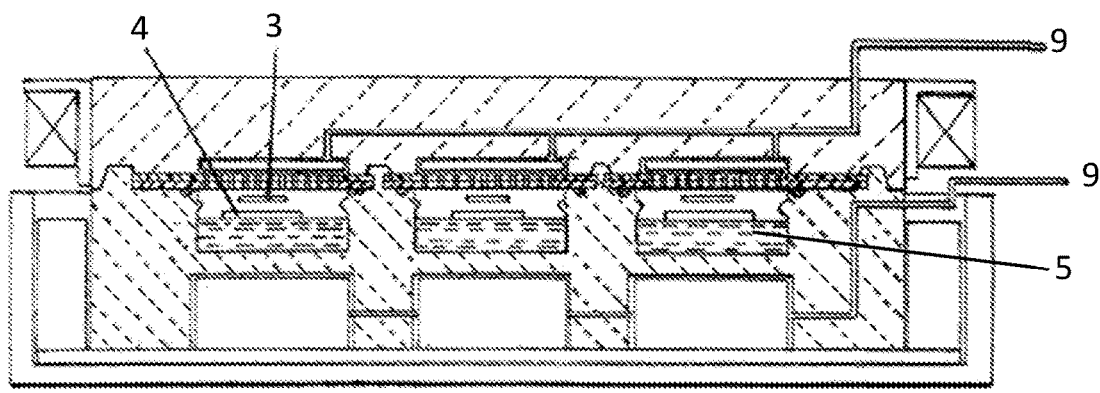
Figure 3:
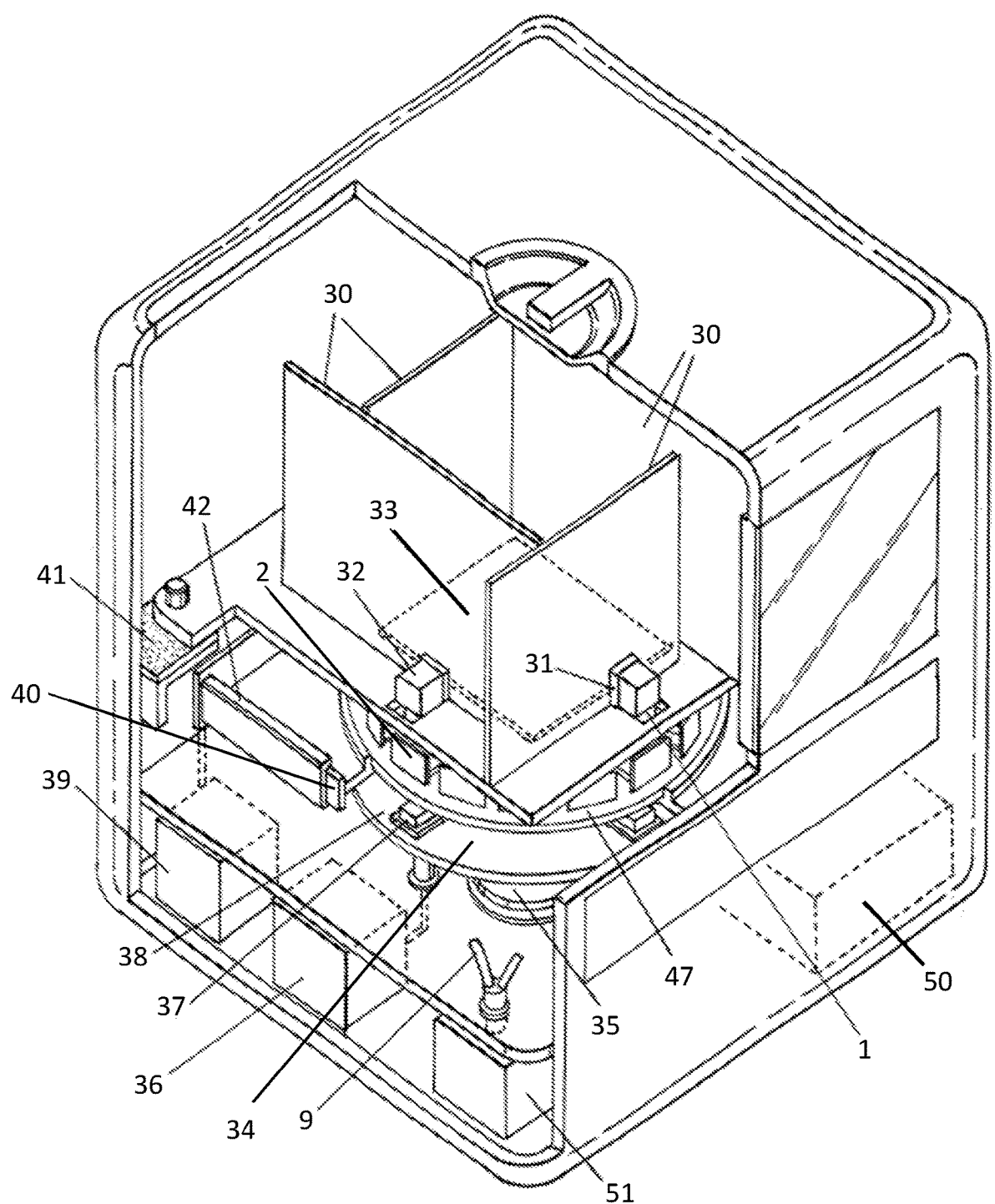
FIG. 3. The device is pictured in a cube format. Four PC boards 30 are shown connected through a pin coupler 31 to the electronic box 32 to a nanosensor 1. An elastomeric pad 33 is shown as a roof over a well plate disk 34. A well plate rotation motor 35 rotates the well plate 47 over the well plate disk 34 to set a sample well 2 beneath a nanosensor 1. An optional battery 50 may serve as main power or backup power. A lift plate servo motor 36 lifts the heater blocks 37 disposed on a lift plate 38 to heat a rotated sample under the electronic box 32. An air pump 51 controls flow of gases through air portal lines 9 into and out of the device. A drawer slide motor 39 opens and closes a drawer 40 for sample insertion and removal. An elastomeric seal 41 seals the device when the drawer slide 42 has closed the drawer 40.
Figure 4:
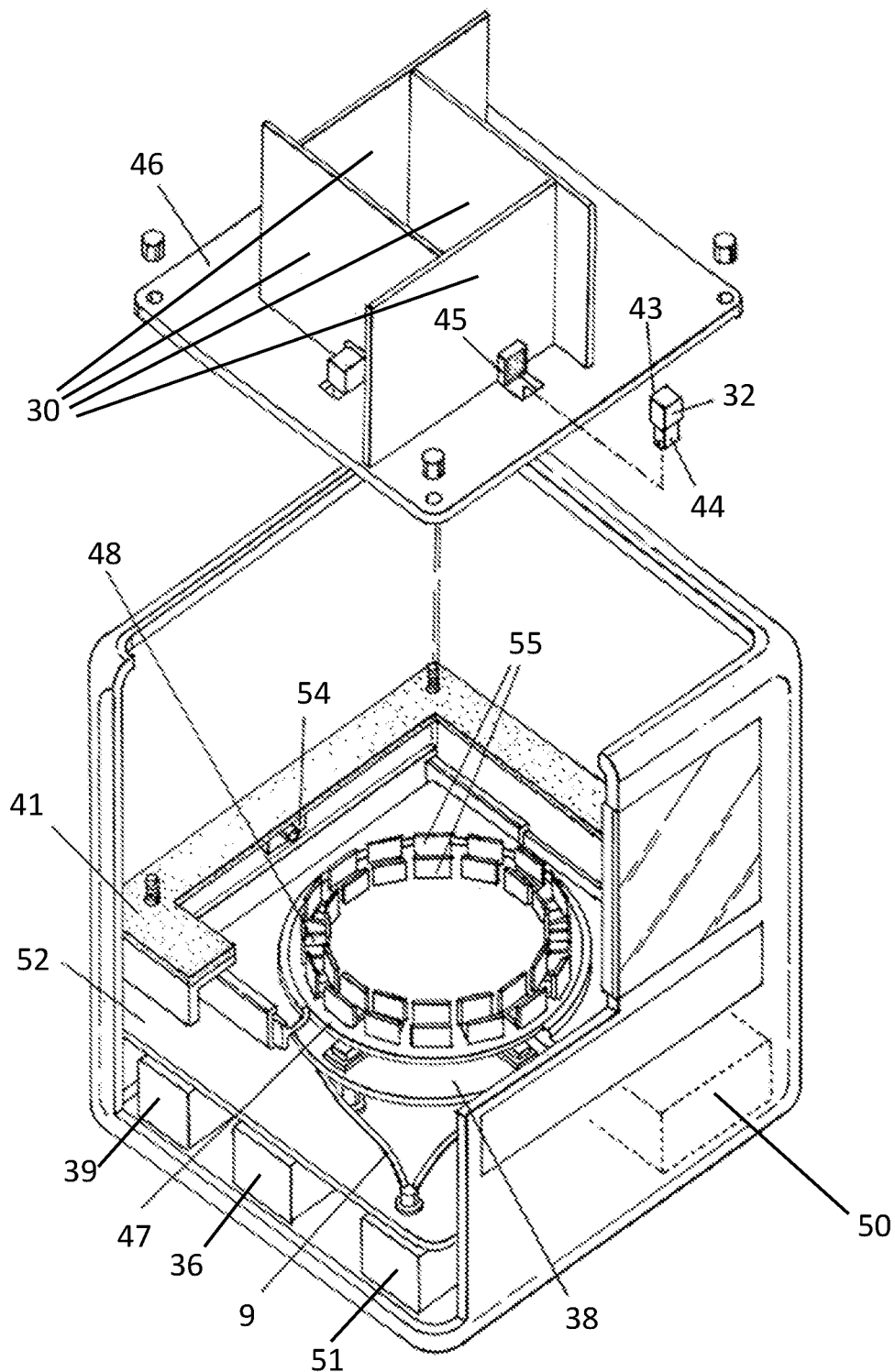
Figure 5:
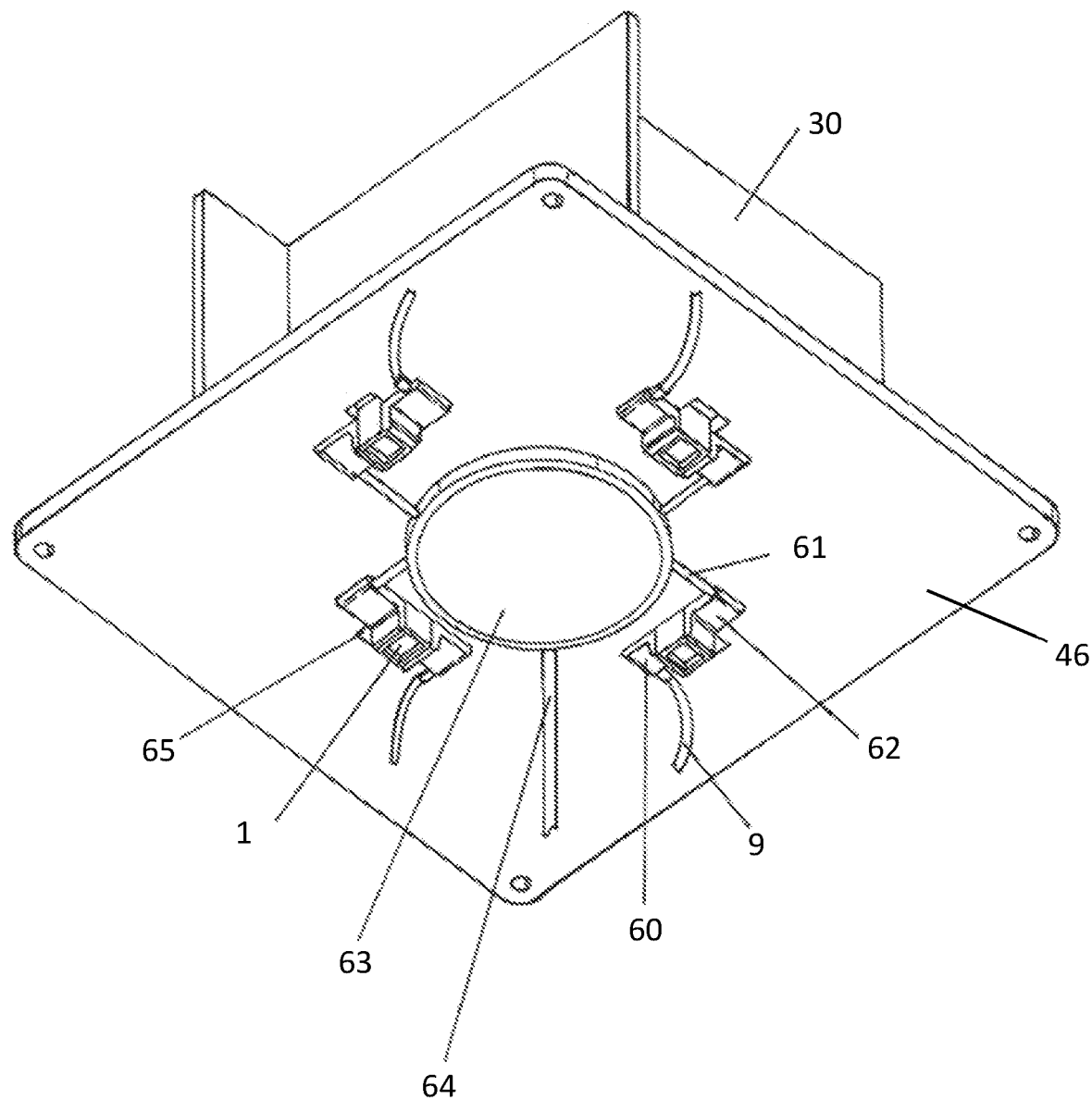
FIG. 5. An underside view of a nano sensor plate 46 is illustrated. The PC boards 30 are shown above the nanosensor plate 46 with nanosensors 1. An air line 9 is shown connected to an airline duct 60 adjacent to a nano sensor 1. A suction line 61 draws gas through an air outlet duct 62 to a sterilization chamber 63. A exhaust line 64 exits the sterilization chamber 63. A gap 65 is shown to illustrate interchangeability of nanosensors within the device.
Figure 6A:
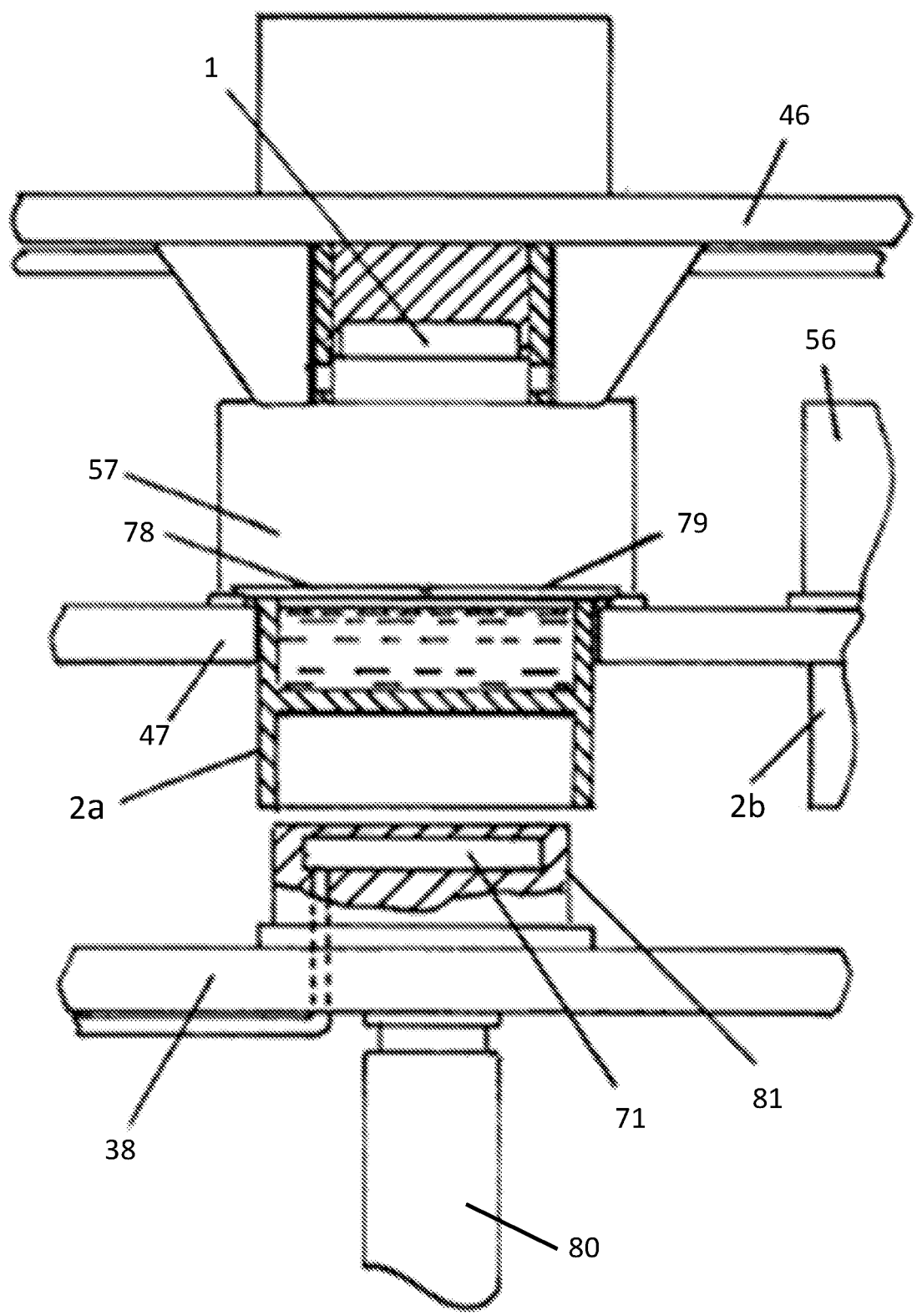
FIGS. 6A and 6B. A portion of the well plate well station 2 as found in FIGS. 1-3 is shown in greater detail.
Figure 6B:
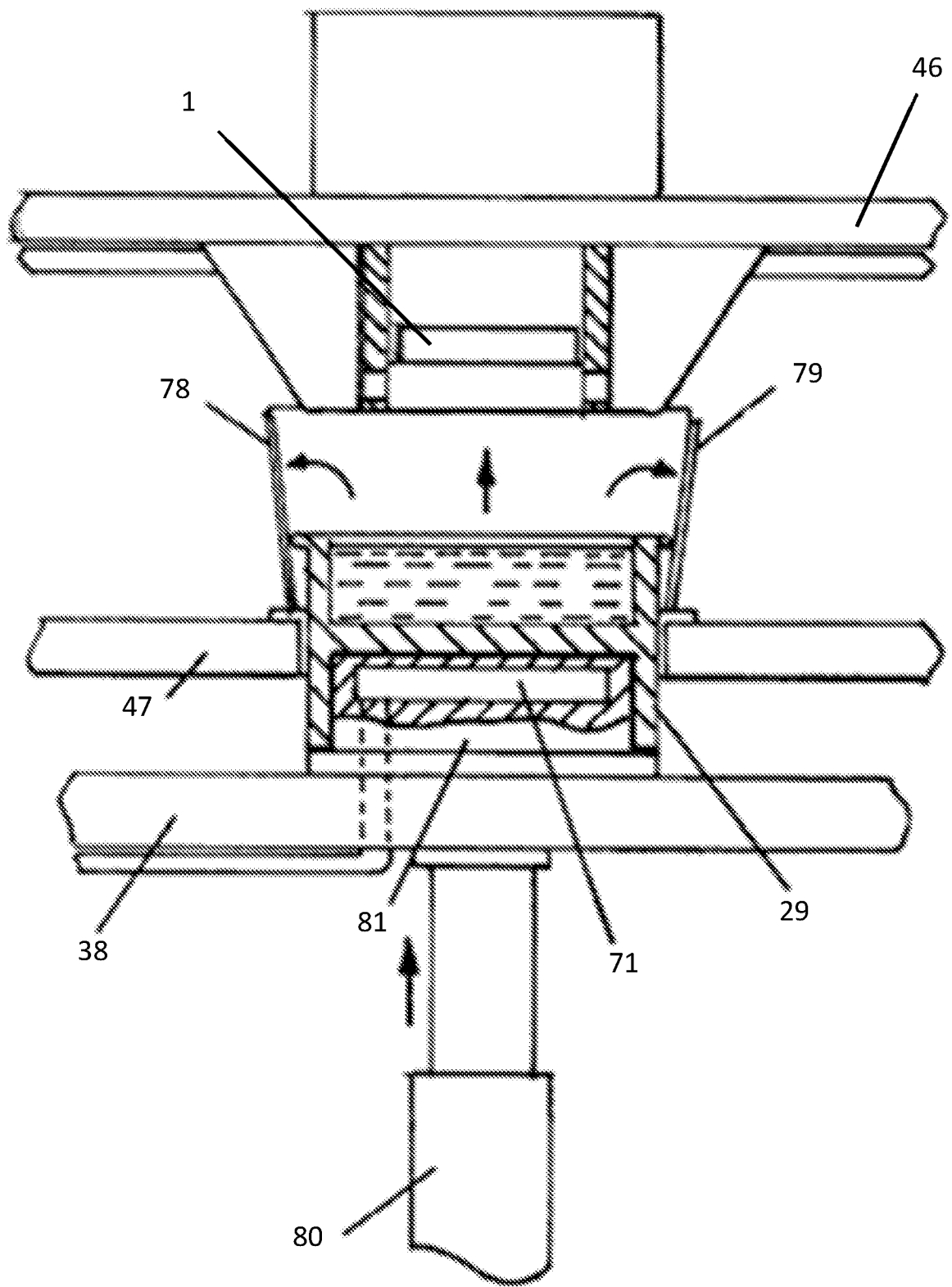
Figure 6C:
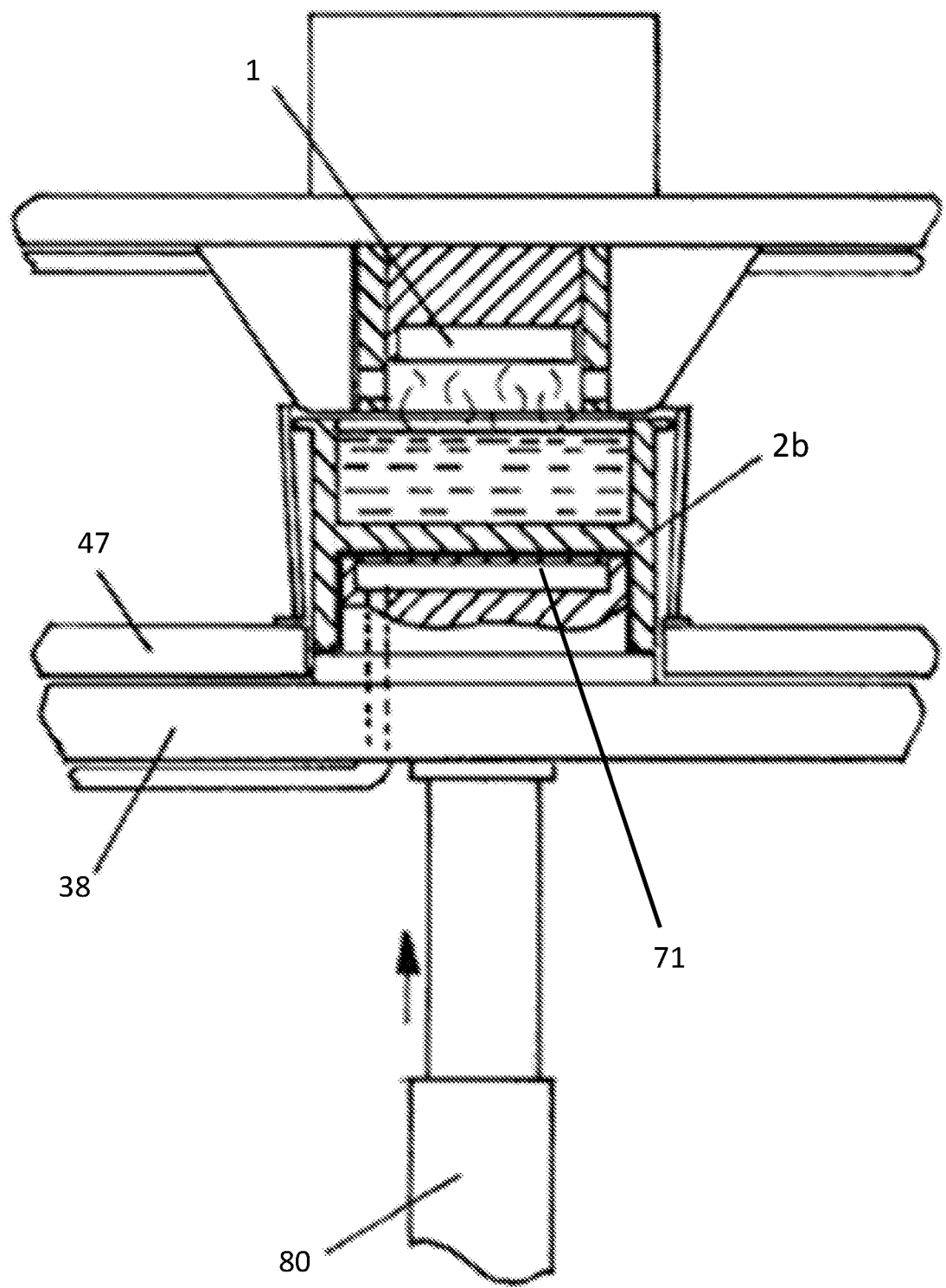
In FIG. 6C, Well Lifted to Nano Sensor, the heater 71 in well 2 2b has been raised by the piston 80 and lift plate 38 through the well plate 47 is shown to have abetted volatilization of compounds delivering them to the nano sensor 1. While in FIG. 6D, Lift Plate Drops, Air Cleans Nano Sensor, a flushing operation is shown in well 2a with the piston 80 retracted to lower the lift plate 38 and the heater 71 to no longer heat the void beneath the nano sensor 1 across which air in 74 and air out 76 are showing a flushing operation through entry duct 75 and exit duct 77. Panels 1 78 and 2 79 have returned to their closed positions. The arrows in FIG. 6D show movement with respect to FIG. 6C.
Figure 6D:
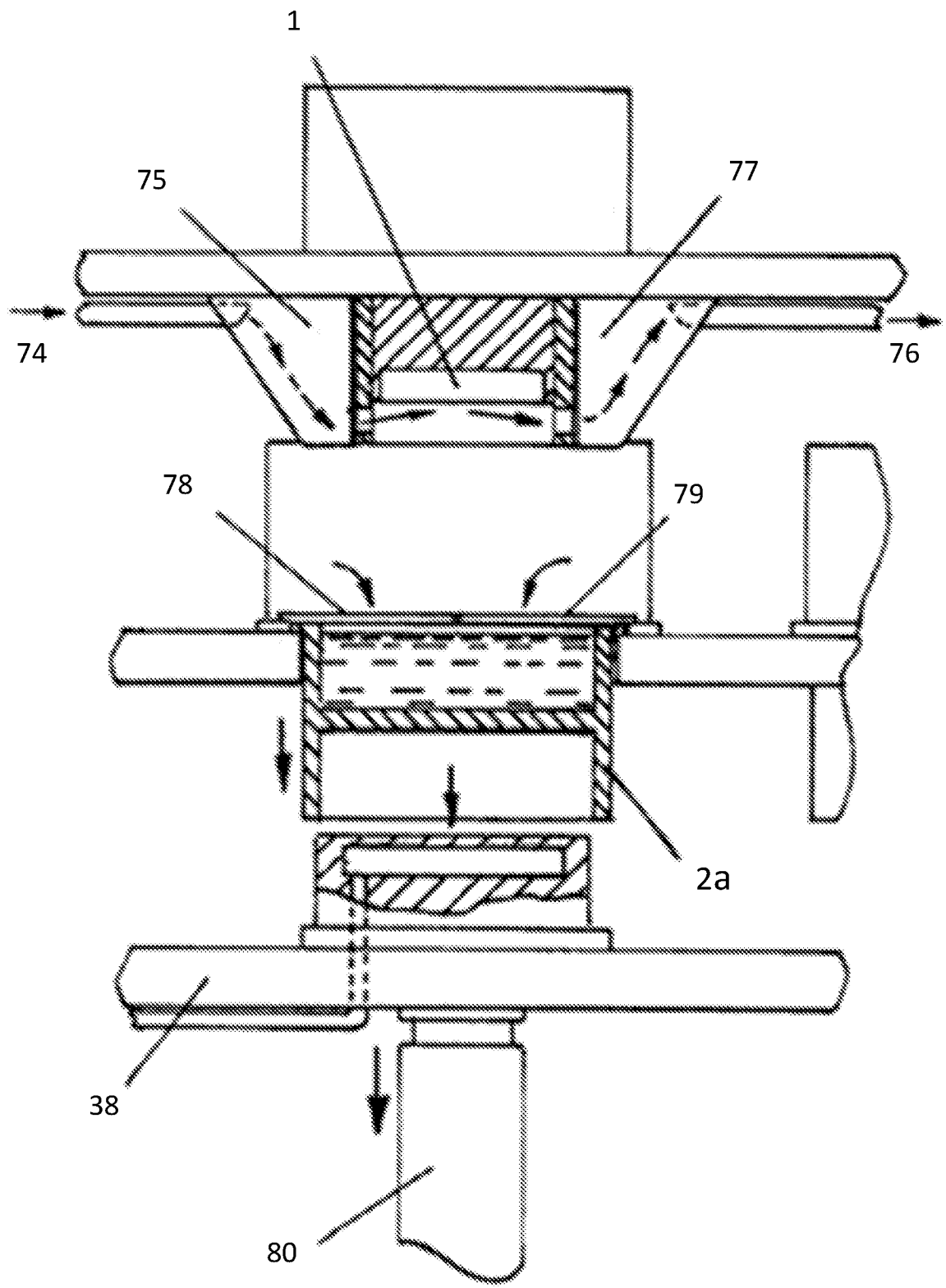
In FIG. 6E, Motor Indexes Next Well to Nano Sensor, a drive shaft 90 passes through the center of the lift plate 38 to rotate sample wells 2 on well plate 47 to the next station. Well 2 2b is shown adjacent to well 3 2c. These are two of the sixteen sample wells 2 on a sample well plate 47. Four rotations, each rotating the sample wells 2 one position will have delivered each sample to a sampling position. In a circumstance where the four nanosensors 1 are each assaying every sample, sixteen rotations of 22.5°, 1/16 of the arc, will result with each sample well 2 being assayed by each nanosensor 1. Arrows show movement directions.
Figure 6E:
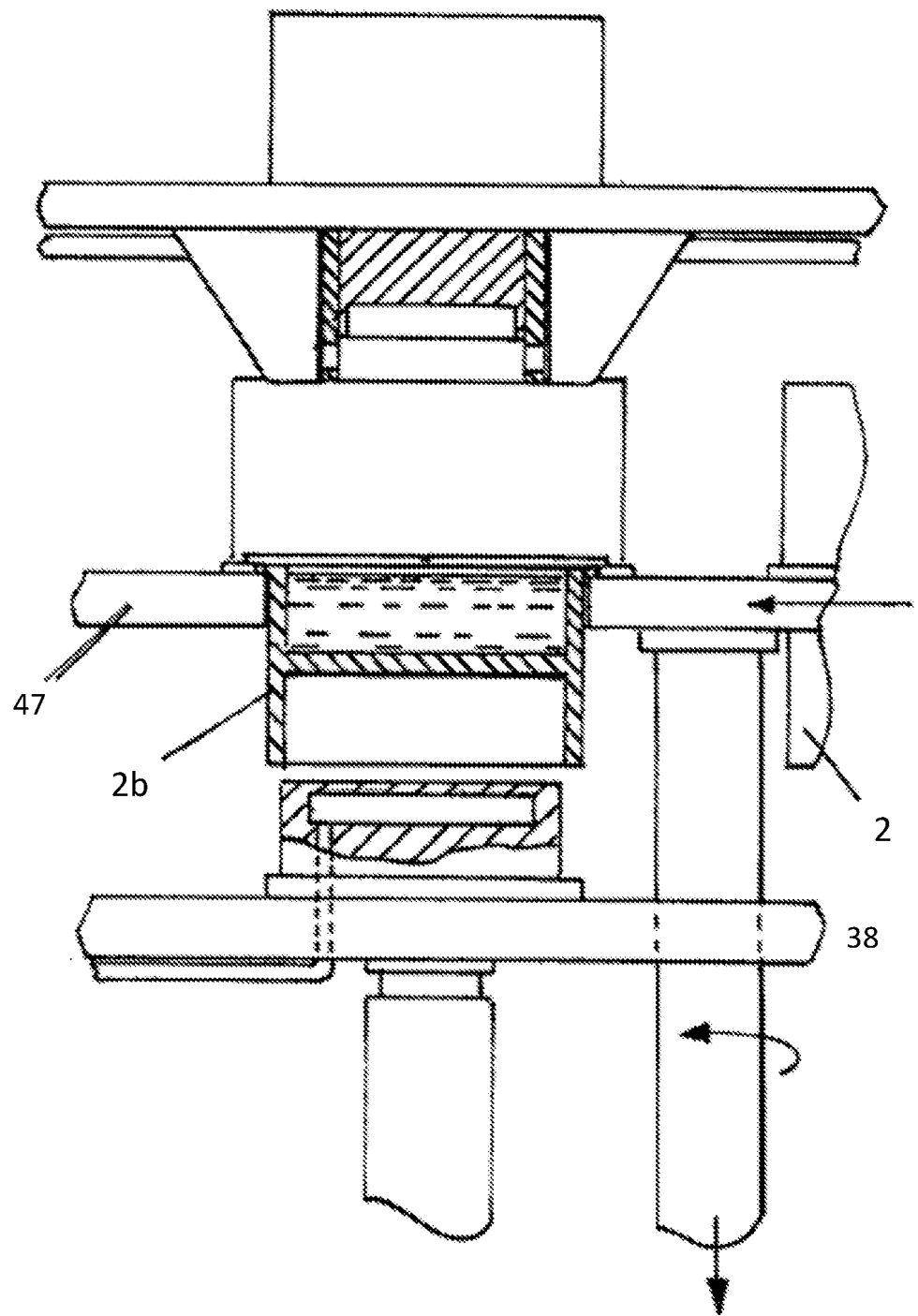

Depending on delivery method and me of residence in the assay chamber, a sampling rate of less than 1/min is currently achievable. Sampling rates of about 1/sec per sample are possible. Longer sampling periods, perhaps up to 10 to 20 minutes, may be used during optimization of a newer testing protocol. The speed logistics may be impacted by the rate at which samples can be collected and delivered.

Pressure differential, released gas, vibration and sonication are common formats for physically stimulating and moving a sample. Electromagnetic stimulation may comprise visible or non-visible wavelengths. Laser stimulation allows fine control of intensity and targeting. Physical and/or electromagnetic stimulation may modulate temperature; resistive heat coils, hot plates and liquid radiators are additional options for heating or chilling a sample. Forces including, but not limited to those of: photo momentum, acoustic, gas flow, magnetic, electromagnet, electric, Lorentz force, chip replacement, etc., effects can be used to control movement of sample compounds.

Stimulation may be constant, may be ramped or may be paused, pulsed or increased in time or intensity as the analysis requires. Changes may be linear or non-linear, and in practice can be programmed to any desired pattern. Multiple stimulation types may be used in parallel or in series and may be pulsed or varied between types with each type independently controlled. In some analyses, stimulation for a desired me/intensity may be employed to flush, for example, high concentration volatile components, from the sample or to fragment or combine sample constituents.

Temperature may be controlled by a heater in contact or close proximity to the chip or through controlling ambient gas temperature. A heat source, such as a heater plate may be set to a static excitation temperature or may be variable, for example capable of ramping or cycling to control vapor pressure of components in the sample(s). Each element on the chip may be heated or cooled individually when heating or cooling elements are incorporated in or disposed in conjunction with the NSE. A temperature higher than normal ambient or room temperature will often be used on at least a subset of sensor elements. A sensor element, group of sensor elements, group of activated sensor elements, or the entirety of active sensor elements may be heated (or cooled) to a stable or controlled varying temperature in a preferred range from about 4° C. to about 65° C. The elevated temperatures should be selected with consideration for the decorations on the heated sensor. For many applications a more preferred temperature will fall in a range from about 32° C. to 50° C. Temperatures in the range of the axillary or oral human body temperature of about 35° C. to 38° C. will have some advantages given that most relevant VOCs will be stable and volatile at these temperatures. Temperatures about 40° C., 42° C., 45° C., 48° C., up to about 50° C. can produce exemplary results. In a chilling mode, preferred embodiments store, deliver, and potentially assay the sample to decode its VOC signaling at about 2-4° C., especially for retention or storing, up to about ambient or room temperature. an intermediate temperature, especially, but not necessarily, an increasing temperature from about 5° C., 8° C., 10° C., 15° C., 18° C., or a little higher will temper delivery of VOCs for a time dimension analysis and may improve signature reliability. The specific numbers are not to be read as limiting the scope of the invention or claims. These numbers are to provide suggestions within preferred ranges that set as a a practitioner may target. Targets within the suggested ranges, targets between, and targets flanking the suggested values are within the scope of this invention. The skilled artisan will understand that increased temperatures might degrade some decorations or actually decrease the adherence and electronic sharing between decoration and chip. Embodiments may include a chamber to accept a sample and where temperature, electromagnetic stimulation, physical stimulation, chemical stimulation, etc., may augment delivery or or advantageously modify sample product for analysis.

A chip may be formed in any desired configuration. For example, a 10×10 sensor array on a chip can provide a compact yet exuberant surface. Arrays may be constructed to align with squares or powers of 2 as is common in computation devices and some biological plates. Thus, for some embodiments a 2×2 sensor chip may be sufficient. But more often a greater number of chips will be employed for additional sensitivity and discrimination abilities allowing assay results to be collected on a greater number of analyte chemicals. Thus, a 3×3, 4×4, 5×5, 6×6, 8×8, 10×10, 12×12, 15×15, 16×16, 18×18, 20×20, 25×25, and so on, including intervening squares, mentioned and envisioned here, but not exhaustively incorporated in the text format might be constructed. Other non-square formats are also envisioned. In biology plate sizes based on a power of 2 times 3 are often employed. Thus 48 well, 96, well plates, etc. are common and easily handled by modular software applications. Since binary electronic electronics often increase capacity according to powers of 2, but physical dimensions may not always be supportive of such doubling with each improved version. Software may often be capable of addressing a number in excess of the NSEs on a chip. For example, computations relating to $2^6$ may be used with a 7×7, 8×7, or 50 element chip. A 10×10, i.e., a one-hundred element chip may be served by an application designed for up to $2^7$ (128) element channels. Higher element chips may thus suggest using applications that have capacity for $2^8$, $2^9$, $2^{10}$, $2^{11}$, $2^{12}$, $2^{13}$, $2^{14}$, $2^{15}$, $2^{16}$, $2^{17}$, $2^{18}$, $2^{19}$, $2^{20}$, etc., NSE channels. The chip may be configured with one dimension far in excess of the other. For additional capacity or perhaps to consolidate assay functions in between bulk restoration functions, a chip may be configured in a flexible format in the form of a ribbon with a fraction of the length presented at each analysis function. For example, several 12×8, 10×10, 12×12, 20×20, etc. analytical portions might be exposed with the ribbon being advanced for each subsequent analysis round. A mask may be used to expose only a portion of the chip, for example to select a class or classes of decorations for different exposures to sample VOCs. Such mask may be perforated and moveable allowing multiple reads on a portion of the chip without need to restore or advance the chip after each assay or assay condition. A mask with perforations can be made to allow for multiple sensor layers to reside on a chip. For extra high throughput, the ribbon may be advanced in continuous movement where samples are presented at a high rate, perhaps 1/sec. The just used portions of the ribbons may be restored in series with assays by passing through a restoration chamber or may be constructed as a disposable cartridge.

A restoration or cleansing step associated with each analytical round might involve a continuous cartridge or band, where, for example, the assay is accomplished in the assay chamber and when the band is advanced, it passes through another chamber, possibly with a different ambient gas at a different temperature. The chip temperature might not itself be specifically or self-controlled in this format; the ambient gas could provide the thermal energy releasing the assayed compound from the NSE. An atmosphere different from that in the sampling chamber might be used in the restoration phase. Bulk restoration, for example, at the end of a shift might be desired in some circumstances.

The ribbon may be a rigid or semi-rigid strip or might be flexible so as to be compactly spooled. As costs of the NSEs decrease, ribbon formats may be desired and permit disposal after use.

Then NSEs are preferably extremely compact in size to permit high density and smaller device footprint. NSEs on a chip will be separated from neighbors by insulation barricades. Many insulators are known and can be selected during design based on parameters such as appearance, size, cost, assured availability, etc. Polyamides are common inexpensive insulation barricades. Circuit board material (e.g., FR-4, CEM-1, CEM-3, RF-35, halocarbons, fluorocarbons, Teflon®, PTFE, polyimide, etc.) is also a strong candidate for use in high production models. Depending on material and anticipated voltages, an inter-element separation of ~50 nanometers (nm) is often sufficient. Larger voltages may require greater isolation distance between elements. The elements themselves may be any desired shape, e.g., rectangular, rhomboid, hexagonal, triangular, elliptical, circular, irregular, crumpled, creviced, shredded, perforated, layered, masked, etc. Sizes can be miniature, e.g., ~40-50 nm thus suggesting the term nano-sensor. Size is a simple design consideration involving, e.g., manufacturing efficiency, device dimensions, density of sensors, surface to volume ratio of NSE, sensitivity of detection, durability, cost, etc. Accordingly, sizes of elements may be in the area of for example, 40 nm, 50 nm, 75 nm, 100 nm, 200 nm, 250 nm, 500 nm, 0.5 µm, 1 µm, 5 µm, 10 µm, 50 µm, 100 µm. Shapes may be planar, essentially flat on the substrate surface, or at an angle disposed off the surface. Shapes may be irregular, e.g., crumpled or creviced. Shapes may be regular, e.g., hexagonal, creviced, etc. A sensor element disposed on and above a substrate surface may be designed as such to increase or maximize surface area to interact with the vapor that may or may not include a VOC of interest to said sensor.

Although larger elements do not cease to function, the advantages of smaller size generally outweigh advantages attributed to larger element size.

The elements will generally be supported on a non-conductive substrate like Si.

VOCs in Contact with the Chip Sensor Elements

As designed, the NSEs do not contact the sample itself, only vapor or gaseous phase emissions off the sample are available for contact. Vapor constituents, as the vapor flushes through the sampling chamber, will specifically bind to one or more of the decorations on the NSEs. Depending on temperature and possible gas or combination of gases used as ambient atmosphere, the collated NSE data produce a characteristic response for a specific VOC, combination of VOCs, or class of VOCs. A chip generally will be coated with several types of sensor elements whose sensing specificities are distinguished by having different decorations such as nucleic acids attached on their surface. Polyaromatics, heterocyclics, and aromatic peptides, including synthetics, may also be valuable decorations. Differential specificity of a chip element may be exhibited at different temperatures, in different atmospheres and/or in different sequence patterns of exposure.

Temperature is significant for at least three important reasons. One, at higher temperatures, the molecules will have higher kinetic energy and thus be less likely to sit docilely on a surface. Different VOC compounds will exhibit different specific temperature effects as will different decorations. Two, the actual VOC chemical may tautomerize or morph, perhaps with a higher temperature favoring a different bonding structure than a lower temperature. A compound might then, in some embodiments, be detected on different NSEs at different temperatures. Such assay response may be used to more specifically identify and assay a particular compound. Three, improper temperature management can comprise sample integrity, for example, leading to clumping, particulate contamination or other sample degradation.

A sample may be introduced into the testing chamber and maintained therein while a change in temperature alters the sensing specificities of the elements on the chip(s). In embodiments where individual sensors have dedicated temperature controls, NSEs with identical decoration, but read at different temperatures can provide the temperature differentiation analysis more rapidly, i.e., without waiting for a temperature change on the entire chip thus aiding in high throughput analysis.

In general, the interactions between the sensing portions of each sensor and the sensed analyte are low energy bondings or coordination complexes between organic molecules. Bonds do not involve covalent reactions and thus are reversible by changing the conditions in the chamber. Dilution, i.e., simply flushing, in many circumstances will ready the sensor element for its next round. Optionally, a different gas is used for flushing and/or a higher temperature may be used. In addition to thermal or convective restoration processes, any format used to physically move the compounds can be used alone or in concert with others to excite/remove the panoply of complexed VOCs. Forces including, but not limited to those of: photo momentum, acoustic, convective gas flow, magnetic, electromagnet, electric, Lorentz force, chip replacement, etc., effects can be used to prepare for a subsequent sample read. Non-convective restorative forces will be especially advantageous in low pressure, or no added gas embodiments. The broad spectrum of restoration options enables testing of multiple samples types in high throughput operations.

EXAMPLES

On a chip, a simple configuration in binary format comprises an element grid arranged in a 16×16 ($2^4 \times 2^4$) pattern, i.e., 216 ($2^8$) elements. Larger chips generally but not necessarily may follow a continuing binary pattern, i.e., 16×16 (256), 32×32 (1024 or $2^{10}$), 64×64 (4096 or $2^{12}$), 128×128 (16,384 or $2^{14}$), 256×256 (65,536 or $2^{16}$), etc. A chip need not be square, e.g., 4×16, 4×32, 8×16, 8×32, 8×20, 4×5, 5×17, etc., etc., etc., are discretionary choices. A chip may be oblong or radial, triangular, etc. For example, a first row of sensors may be a single sensor, subsequent rows may be 3, 5, 7, 9, 11, 13, etc., respectively. A first row may have x sensors, with subsequent rows having, for example, about 1.5x. 1.5x, 3x, 3x, 1.5x, 1.5x, 1x. The pattern of sensors on a chip is at the discretion of the designer. A temperature higher than normal ambient or room temperature. A temperature higher than normal ambient or room temperature will often be used on at least a subset of sensors. Embodiments may use temperature, electromagnetic stimulation, physical stimulation, chemical stimulation, etc. to deliver or modify sample product for analysis.

A chip may not use all elements as active NSEs. Some may be inactive, some may be held in reserve, some may serve as controls or calibration elements, etc. The chips are functionalized or "decorated" single wall nanotubules (SWNTs). Nucleic acid molecules are inexpensive decorations that can be made with thousands of options. Using non-natural, i.e., nucleic acids not in the human genome or RNA repertoire, many more specificities can be addressed. Synthetic polymers mimicking the DNA decorations may be selected without attention to avoiding toxicity. In fact, toxicity of a ring or ring family may be favored as this suggests bioactivity, i.e., ability to bind organic compounds. Heteroaromatics that may be incorporated into decorations as, e.g., substitutes for natural purine (guanine, adenine) or pyrimidine (thymine, uracil, cytosine) in a polymeric functionalizing group include but are not limited to: 4, 5, 6, 7, 8, 9, 10, or higher member rings, also including polycyclic structures. Thousands of heterocyclic compounds are known in the art. Decoration compounds comprising residues of molecules including but not limited to: furan, tetrahydrofuran, pyran, dioxanes, oxepane, xanthene, dibenzofuran, strychnine, tetrodotoxin, pyridoxine, biotin, thiamine, folic acid, riboflavin, aflatoxin, acridine, pyridazine, pyrazine. pyridine, indole, isoindole, carbazole, indolizine, quinoline, isoquinoline, azecine, azonane, azocine, azocane, oxazole, isoxazole, thionin, oxathiolanes (e.g., 1,2-oxathiolane)silole), pyrrole, trimethylene sulfide, etc., are available for functionalization. Such residues may be incorporated in or attached to nucleic acid decorations. Amino acids with ringed structures can also be incorporated as functional coordinating binders. Thus, specificities of NSEs are tuned to the desired conditions. Sometimes the identical decoration will display different specificity as temperatures change.

A base voltage of generally is in a relatively low, i.e., non-arcing or insulator damaging range for example in an order of magnitude around $10^0$ pV, $10^1$ pV, $10^2$ pV, $10^0$ nV, $10^1$ nV, $10^2$ nV, $10^0$ μV, $10^1$ μV, $10^2$ μV, $10^0$ mV, $10^1$ mV, $10^2$ mV, $10^{-2}$ V, $10^{-1}$ V, 1 V, 10 V, but up to 20 V, 50 V, even 100 V, when care is taken to prevent arcing, is applied to an input electrode of a sensing element. $10^{-18}$ amp is a minimum amount sensitivity with 0.4 fA being characteristic some current implementations. The voltage provides an electric field that may attract or repel portions of a VOC and thereby determine the length of time and phases of association between a VOC and the proximate sensor. The electric field may orient or reorient the VOC as it approaches, interacts with, and leaves the sensing zone. Reorienting, i.e., twisting or bending responses of the VOC will help to distinguish it from other VOCs. A sampling rate adapting to these interactions is thus preferred. Samples about every 5, 10, 20, 50, 100 μsec thus offer a advantageous distinguishing ability over slower sampling rates. Sampling frequencies in the kHz range, for example, about: 200 kHz, 120 kHz, 100 kHz, 80 kHz, 60 kHz, 50 kHz, 40 kHz, 30 kHz, 25 kHz, 20 kHz, 18 kHz, 15 kHz, 12 kHz, 10 kHz, 8 kHz, 5 kHz, 2 kHz, 1 kHz, 0.8 kHz, 0.5 kHz are within a preferred range. An interactive controller, for example, increasing sampling rates for elements sensing a change (i.e., approaching or proximate VOC) increases efficiencies of the supportive hardware and signal processing.

The voltage may be static or oscillate (either deterministically or stochastically). Oscillation may include ranging from positive to negative voltages, may include simple on-off switching or other square wave pattern, saw tooth pattern, triangle pattern, stochastic, etc. Voltages may be stepped through a range or introduced in a ramping or cyclic (e.g., sinusoidal) pattern or stochastic perturbation. Voltage may be sent to each sensing element individually or the same voltage may be applied to several sensors, including circumstances where all sensors are fed identical input.

In the NSE, current is or is not delivered from an input electrode to a corresponding output electrode through a field effect transistor carbon layer. In one set of examples the carbon layer is formed as a single walled carbon nanotube (SWNT) layer. In the on mode, the SWNT carbon conducts a current through to an output electrode. When the field effect transistor is in the off mode, the current does not conduct. Several such elements are attached to form a nano-sensor chip. The conductance of the SWNTs on the elemental surface is perturbed by close association with a target compound, for example a volatile organic compound. Binding of such target compound modifies conductance of the SWNTs in such a fashion that the coordination binding acts as a transistor switch turning the gate on or off. In some instances, the coordination will be probabilistic with rapid gating as different portions of the target compound may bind to the SWNT, perhaps at slightly different coordinating atoms. Such probabilistic binding may be temperature or voltage dependent or may vary with the delivering gas. In other instances, the binding may be more constant, simply gating for a range of temperatures/voltages with large zones of on or off signaling.

Specificity

Specificity of coordination is provided by functionalizing or decorating the carbon gate electrode. For example, many sequences of nucleic acid such as DNA or RNA will stringently coordinate or bind with the SWNT structure. These nucleic acids may be naturally occurring or synthetic. The ringed structures of the nucleic acids or other molecules such as peptides containing a large fraction of ringed structures (broadly referred to as aromatic polypeptides) associate strongly with the nanotubular structures and organic compounds. These functionalizing or decorating additions to the SWNTs serve to selectively capture (i.e., slow or stop the movement of) proximal molecules by association using intermolecular forces, e.g., dipole-dipole, induced dipole, Van der Waals, and sometimes ion-dipole interactions. When the chemical (electron distribution) geometry is thus changed, the gating characteristic of the associated carbon bridging the input and output electrodes is modulated. A single element may be associated with a single sequence or a plurality of functionalizing sequences. Different decorations themselves will have attractive proclivities for a set of VOCs different from those associated with other decorations. A plurality of decoration compounds is advantageous for differentiating between different VOCs. Other means of changing sensor-compound interactions, e.g., temperature or voltage of the sensor element, may be employed as alternative differentiation tools, but preferably are used in conjunction with a chip comprising a plurality of decorations. The differentiated sensor elements may be arranged in zones on a chip. For example a first decoration may be present in a 4×16 zone on a chip. A second decoration may appear on the chip linearly at the end of the first decoration. A third, fifth, seventh, ninth, eleventh, thirteenth, and fifteenth may appear in subsequent 4×16 columns adjacent to the first decoration. A fourth, sixth, eighth, tenth, twelfth, fourteenth and sixteenth may appear in 4×16 columns across from the second decoration. In an exemplary embodiment, rows 1-4, 9-12, 17-20, and 25-28 are controlled to be at temperature A; while rows 5-8, 13-16, 21-24, and 29-32 are controlled to be at temperature B. In this example with 16 different decorations on the sensor elements, 32 different recognition formats between VOC and sensor are present with 32 occurrences of each format. As a refinement to this example, the odd columns are set with a base voltage Y; while the even columns are set with a base voltage Z. In this refinement 64 recognition formats are available with 16 occurrences of each. The multiple occurrences improve the likelihood of a VOC molecule associating with that sensor element type. The number of different decorations can be modified as a design choice. rather than a $2^5 \times 2^5$ chip size the practitioner may elect a size in accordance with preference or designed specifications. A $2^4 \times 2^4$, $2^6 \times 2^6$, $2^x \times 2^x$, $2^x \times 2^y$, or other configurations are arbitrarily selected in design to comport with desires or limitations for the device. While powers of two are chosen for ease in describing these examples, the device is not limited to chips having these architectures. Where the above examples illustrated two temperatures and two voltages, the device may have, e.g., 1, 2, 3, 4, 5, 6, 7, 8, 9, 10, or more different temperatures or voltages in a static operational mode. In a dynamic mode, the temperatures or voltages may vary in accordance with a predetermined, operator determined, or algorithmically determined pattern.

Output characteristics of gating in response to one or more gaseous compounds, e.g., VOCs are then collated into a data library. When that NSE responds in the same manner, presence of the VOC is confirmed. Stringent selection of element functionalizations, and subsequent application of the controllable assay variables can optimize certainty of VOC identification at a desired level, for example, increasing manipulation of the variable parameters can achieve certainty of 99+%. In special circumstances, for example to develop rapid profiling of a new VOC signature (i.e., pathogen), a simplified screening protocol or developmental process may begin with a lower level of certainty, e.g., 85%, 95%, etc. Subsequent refinements then could be applied to raise the level of certainty until reaching a mathematical and chemical sensitivity to an acceptable level, e.g., a 99+% certainty.

A single element may be capable of indicating the presence of more than one compound. For example, similar compounds may not be distinguished in their association/coordination with the element surface and therefore may in certain circumstances produce indistinguishable signals on their own. But the single element may, for example, in conjunction with one or more other elements provide definitive results with respect to the VOCs that may interact with any one element. Alternatively, the single element when operated at a different temperature, voltage or other variable may distinguish between the different compounds binding the element under static conditions. The discussion above describing the variable inputs and input patterns and different resulting outputs relates to such differentiation capabilities.

Fast Tracked Testing and Reading

One embodiment may include a simplified assay, perhaps a chip with fewer component element or element types, e.g., using only a fraction of the DNA species on the general use chip. In simplified embodiments fewer parameters may be manipulated, perhaps a static system where one or more variables, such as, voltage, temperature, etc. have a reduced range or remain constant. When AI identifies, for example, a simplified signature for a specific set of diseases or a specific disease, such as a new virus or strain of virus, the device may be instructed to operate in a simple detection mode similar to that of a +/− strip test. Chips may thus be made specific for different preferred assays or a regular chip may be used with simplified readings.

A simplified data analysis may be inherent in the chip. For example, a circuit can be built with specific sensors in series and/or in parallel. When the circuit produces the right gating, a positive result would be output. A side circuit on the chip possibly sharing portions of the positive negative circuitry may be included as a control. In some embodiments a completed control circuit with an incomplete or open positive circuit may produce a "negative" signal. The chip itself may contain a coded instruction for the machine to operate in the designated mode, e.g., an optical patch, physically slotting, an RFID, actual machine readable code, etc., may instruct the machine to operate in the preferred program manner. Such a streamlined approach can enable extremely high throughput analysis of targeted profiles.

Shielding

As sensitivity is heightened, machine stability becomes more important. Therefore, depending on output sensitivity targets, formats of samples, formats of delivering the samples, etc., shielding is considered a major design consideration. For example, if acoustics are used to advance, modify, present, or to remove samples, acoustic shielding in the relevant wavelengths and consideration of harmonics of the structural hardware, should be taken into account during design and installation. Passive, e.g., sound insulation, or active, e.g., sound cancellation shieldings are compatible with such shielding requirements. Electromagnetic shielding can be any suitable format, e.g., conductive material such as copper, nickel, mu-metal, conductive plastics, conductive paints/inks, etc. In general, the device should be protected or shielded from any influences, that interfere with performance including, but not limited to: acoustic, temperature/thermal, electromagnetic, visible, infrared, ultraviolet, radio/micro waves, magnetic, electric, etc. For particular environments, including, but not limited to: space travel, zero or low gravity, proximity severe weather events, deep sea or deep underground, high altitude, atmosphere, where the device is to be used, additional shielding, e.g., from heat, ultraviolet light, solar wind, ionizing radiation, high velocity transit, constrained environments, densely populated locations, proximity to nuclear power plants or engines, vibration, etc., is a desired design feature. While general ambient conditions for most of the device's intended uses will be relatively standard. When a device is designed for use in any extreme environment, additional relevant shieldings should be studied and applied where appropriate for example when designed for use for a long duration space flight.

Data Storage and Analysis

Raw data may be stored in a library linked to the sample source with any other relevant information including, but not limited to: disease diagnosed, disease status, nourishment history, time of collection, volume of sample, volume analyzed, medical history, preparation steps before analysis, storage and/or chain of custody conditions, medications, gender, age, etc. Such library may be stored or transmitted in any available format and process taking safety, privacy, consent, cost, relevant laws, legal jurisdiction, storage density, transit speed, etc. into account with a goal of interfacing groups of machines in a knowledge base where each device teaches and learns from others. Portions of the library may be stored in diverse locations including any available format, e.g., single encrypted, double encrypted, or block-chain coded.

Files in such library may be compiled and analyzed by knowledgeable humans, but more preferably using machine learning and/or artificial intelligence in any combination. Such processing, analysis and comparing multiple samples with associated information will then be useful for continuous expansion of the disease repertoire and the improvement of diagnostic accuracy and quality of the output data.

Early Warning System

One especially poignant application of this device and technology relates to infection by a virus. Viruses are often specific to a small population of cell types at a particular state of development. For example, in the case of a corona virus such as the SARS-CoV-2 virus that is responsible for the COVID-19 pandemic, the "spike" or S-protein binds to Angiotensin-Converting Enzyme 2 (ACE2) found on human cells. The spike protein also acts in conjunction with another cell surface protein, TMPRSS2, to initiate cell processes causing viral entry. ACE-2 is found on multiple cell types in the human body, including, but not limited to: endothelial cells of the circulatory system, enterocytes of the small intestine an in especially high numbers on Type II alveolar cells in the lung. Type II cells are the cells that secrete surfactant coating the air sac surfaces. Surfactant lowers the surface tension of the fluid coating the alveoli and thus helps to keep air sacs in an open, rather than a collapsed state. When the alveolar cells are targeted and eventually killed to release new virus, breathing becomes more difficult as the air sacs lose air exchange surface area and increase amount of fluid in the lung. This diminished lung function can be diminished further as the immune system gears up to fight off the virus. The immune responses can further fill lungs with fluid and pus and severely compromise breathing. In this example, the type II cells are known for high contents of dipalmitoylphos-phatidylcholine, ethanolamine, cholesterol and many trace organics.

Certain adaptations of ACE2 bearing cells resulting to their adaptations to stresses from obesity, renal disease, cardiac stress, etc. apparently makes these cells better targets for the virus. Lung cells die in high numbers and release contents upon cell lysis and death. Some content is expired in the breath, but most is transported by the blood for processing and removal. When the blood is filtered by the kidneys, VOCs released during cell lysis will be delivered into the urine. The appearance of VOCs in patterns relating to a type II cell origination provides evidence of attack on these cells. Knowing which pathogens are in circulation can increase the certainty that the source is from the SARS-CoV-2 actively pandemic virus. The human, artificial intelligence, and/or machine learning can be more certain when more information is available. For example, persons with the adapted and compromised cells mentioned above will also exhibit breakdown products from these cells in their urine. Assays indicating breakdown products from the non-lung compromised cells can provide stronger certainty that the SARS-CoV-2 is the actual culprit.

Identification of Emerging Biothreats

However, even before a virus is identified, distinct patterns associated with an unknown disease may appear in several samples and be concentrated in one or more locations. This information may help to characterize or identify the unknown pathogen because, when cells are attacked and become infected, they start producing and releasing abnormal VOCs and abnormal levels of other VOCs characteristic of the cell type. Therefore, a network of devices deployed in hospitals (and military installations, factories, airports, laboratories, points of entry, etc.) can act as an early warning system of new emerging viral threats whether natural on man-made. A network and early warning system such as the one described herein can rapidly identify and provide a VOC profile of the new pathogen suitable for use in identification of healthy or infected individuals even before genetically decoded and named. The present invention eliminates the need for genetic decoding testing and development, manufacture and distribution of new testing kits. The device of the present invention does not require special chemical analytical reagents or specially trained laboratory personnel and can be self-administered. When the preferred analyte, urine, is used, only minimal chemical or biolab protective gear is necessary. Therefore, massive scalable testing is enabled using urine (a sterile sample medium without intact pathogens) does not emit particles into the ambient environment.

Each active infective virus will induce specialized responses in the target cell thereby producing a signature pattern of cell metabolism that results in a VOC population highly associatable with the specific virus, sometimes even a specific strain of virus. Each virus requires a receptive cell to endocytose the viral genome and generate copies of new virus. To gain access the virus must bind to a particular portion on a cell. Viruses are thus unique in the cell type or cells types they attack. The pattern of cells and the responses to the attack will be unique to each new virus. So when devices of the invention are interfaced with each other and share data, an early warning wake-up call can identify a potential health risk long before it becomes a crisis or would be recognized following current practice. Through relation to previous data, the algorithms can identify the targeted cells and therefore potential anomalies and treatments related to the cells under attack.

Containment of Emerging Biothreats

Urine samples assayed using the present device can deliver a unique signature profile associated with the viral infection within seconds or minutes of sample introduction. Because the renal system filters blood from all body organs, urine contains metabolic products produced in each organ and therefore will contain VOCs characteristic of the cells under attack. This can help to identify the pathogen in some circumstances, but with new pathogens, by identifying the cells that the viruses use for replication can suggest who is at greater risk and can help in rapidly developing treatment protocols. The rapid identification and recognition of an emerging biothreat combined with massive scalable testing as provided for in the present (networked) invention will enable rapid containment of a geographically designated containment zone greatly reducing the virus' ability to continue its transmission.

Assays under the present invention can recognize a new appearance of previously known signatures or appearance of a previously unknown signature. Geographic location, possibly to a single town, lab, hospital, metropolitan area, zip code etc., will allow instant designation of proposed containment zones. In these zones, rapid testing of associated individuals and contact tracing where relevant can be initiated and accomplished before the numbers of afflicted persons become burdensome or overwhelming. An outbreak, even from a previously unknown pathogen, can therefore be identified and stopped long before reaching epidemic status and hence prevent an epidemic event expanding into a pandemic. In conjunction with the identification and partitioned follow-up of the disease making a first appearance, the disease can be characterized as to source, afflicted cells, possible treatments and/or preventions, etc. Depending on the size and population (and density) of the containment zone, the device of the present invention is modularized to achieve massive scalability from a single unit having a capacity to assay ~500 samples/day to a modularized assortment of networked units with capacity in excess of 1,000,000/day. Rapid deployment to meet the needs of a nationwide emergency or to relieve local infrastructure from being overwhelmed during surge demand is available using prefabricated high throughput assay laboratories outfitted with devices and automated sample management facilities. These automated self-contained VOC assay factories are designed and built to be transportable, e.g., using standard, e.g., ISO sized shipping containers (e.g., 20 or 40 ft, HQ or normal height.). Each of the prefabricated facilities can be deployed using normal transport, e.g., rail, truck, boat, cargo plane or helicopter, to a location in need. The container, depending on circumstance, can be equipped with an electrical generator and supplied with a dedicated accompanying fuel source to supply the generator when warranted, for example, in disaster circumstances. However, the preferred embodiment is to be delivered to and actuated to meet surge demand, for example at a postal facility, a parking lot, a stadium, an open field, on the back of a trailer truck, etc., i.e., wherever is advantageous for optimizing throughput.

In the Covid19 pandemic, to date, urine itself has not been shown to contain functioning virions. SARS-CoV-2RNA assayed in saliva samples is the accepted positive indicator of infection. Less than 10 percent of SARS-CoV-2 positive patients had detectable viral RNA in the urine. So robust genetic tracing of the virus is not possible in urine. Since urine is so commonly available for many bioassays including the presently discussed VOC assays, use of urine as a diagnostic sample and assaying urine VOCs becomes the rational diagnostic/screening method. Fine-tuning signature sensitivity and protocols can be indicative of which patients need more critical care and which may be getting sicker or recovering. A decrease in viral disease signature may be taken as a sign that the host has or has not resolved the infection.

Historically zoonoses, like COVID, have proved difficult to manage. The Spanish flu at the end of World War I apparently jumped from an avian source to humans, likely though a porcine intermediate, in China between 1915 and 1917. This flu was probably carried to Europe by Chinese workers hired to fill in for needed troops. This disease is estimated to have killed between 3 and 5 percent of the human population. Estimates are that as many as one tenth of those infected died from this flu.

Ebola, a viral genus with six recognized species, five of which are infectious in humans, kills between one-quarter and nine-tenths of those infected, depending on species, health of the infected people, and availability of health care. Although Ebola was a known disease, in 2014 the US saw at least a dozen cases, two in health care workers treating an infected patient.

AIDS was a turning point in viral epidemiology. HIV, the virus causing AIDS had low low prevalence in the United States at least dating to the mid 1960s. In the late 1970s and early 1980s the disease skyrocketed amongst sexually active gay men before spreading to others through contaminated needles and blood products. Studies relating to HIV became a starting point for understanding viral sciences in general. The research relating to AIDS or HIV flowed over into other retroviruses and viral disease in general, including the immune responses to these attacks. At first, the disease was not well understood with some theories attributing AIDS to inhalation of nitrous oxide ($N_2O$) whose use was gaining popularity in the San Francisco gay population as AIDS took off. HIV appears to be a zoonotic from a simian source.

SARS, MERS, avian flu, swine flu, represent recent occurrences of zoonotic jumps to humans. These and earlier zoonoses can present with rapid emergence causing severe stress to health care systems (and morgues) with a flux of cases requiring management, preferably including a rapid diagnosis to distinguish the new affect from other diseases and to suggest proper isolations and treatments for those infected. The present invention with a score of cases or fewer can provide a working test profile where those with the disease signature VOCs can be decoded and identified in seconds or minutes. The disease need not be comprehensively or conventionally identified. For example, when a patient presents with symptoms which may be associated with a plurality of diseases, a quick test of breath, urine, off-gas from a hand, armpit, forehead, etc., can categorize the disease as common, perhaps a cold, or as a more serious, potentially pandemic, pathogen.

PREDICT, an epidemiological research program funded by the United States has identified in excess of 1,200 viruses with the potential to cause human diseases and pandemics. These are just the ones "identified". In a Jun. 1, 2018 web posting Andrea Yeager cites: D. Carroll et al., "The global virome project," Science, 359:872-74, 2018 for its reported estimation that 631,000 to 827,000 unidentified viruses exist that have zoonotic potential. This is a large unidentified pathogenic reservoir. The "unidentified" qualification suggests that a specific PCR, antigen, or antibody test cannot be readily prepared. The instant invention is capable of recognizing novel VOC signatures in routine screens, e.g., in a general physical exam, a screen for entry to a facility, a banked blood check, a screen for a pathogen of interest, etc. A few, even less than a dozen, aberrant but matching VOC profiles, especially multiples from a local region or zone can guide officials on applying appropriate screening and control measures.

Cancer

The systems of the present invention are ideally suited for detecting, diagnosing and evaluating cancers. Cancers do not involve all the cells in the body but originate within a specific cell population. As the metabolic activity in the cancer cells is altered, their VOC production changes. Some metabolic changes are common to many cancers. So in some embodiments a signature may be taken as indication of a class of cancers, e.g., epithelial cell cancer. But as signature information is refined the evidence appears to show that even different breast cancers can be distinguished. It is well known that some cancers' responses to hormones is different from other cancers'.

Autoimmune Disease

There is evidence to support that many autoimmune diseases are suitable target for analysis using systems of this invention. In general, a signature immune response underlies the autoimmune cascade. When the attacked cells respond, their metabolisms are particular to the attacked cell type, cell age, location and the like. The specialized metabolisms of the altered cells will produce their particular signature VOC outputs. Thus, VOC analysis in accordance with this invention will be expected to assist in diagnosing various autoimmune diseases.

Microbiome

Another exemplary application is understanding of a person's microbiome. Surface microbes generally emit only trace amounts of VOCs and thus are not yet prime targets for analysis. But ambient gases surrounding an organism may be analyzed to obtain signature information emitted from the skin, whether from the organism or its associated microbiome. In a related set of analyses, since the gut microbiome directly feeds into the bloodstream for filtration by the kidneys this information can be more concentrated and provide a stronger signal. VOCs produced by the organism and the gut microbiome will therefore be present in general analysis. Thus, this microbiome status can be monitored in accordance with the present invention.

Sample Alternatives to Urine

This brings up an alternative application of the present invention. While initial development focused on urine analysis, urine being available non-invasively and in decent volumes; persons also are used to providing sterile urine samples so sample collection is not a confounding issue, the inventor has become aware that inventive technologies are broadly applicable with only minor adjustments. Off-gassing of stool samples can be directly measured. Solid tissue biopsies can be stored and allowed to off-gas into a head space for analysis. The solid sample may be disrupted and liquefied to provide a liquid sample closer to those samples originally conceived. Blood, plasma, lymph, saliva and mucous, though not as readily available as urine are easily obtained samples that are suitable VOC sources for introduction into the device of this invention.

Specialized Applications

Low or Zero Gravity

The device of the invention will be engineered for specific applications. For example, in a weightless or low gravity environment, the random movements of molecules in the vapors will offer significant advantages over devices that assay liquid samples. Collection, storage and feeding of samples into the device will consider the effect or non-effect of gravity, but within the assay chamber and on the chip gravitational effects on the vapor and molecular attraction will be negligible.

The devices and methods of the present invention may serve as a component part of a larger device or larger method. The device is not required to operate in isolation. Data obtained using assays of the present invention may be intercalated with other data, e.g., medical history, age, residence, etc. Additional information may be obtained using the sample being assayed in the primary device of the invention. For example, in an enhanced machine, a capillary analysis system, in series or less preferably in parallel, might be used as one variable or parameter in the data processing to guide analysis along a preferred branch or if used in parallel confirm or question results from the VOC analysis structures.

In another embodiment, a FET or similar sensor system as known in the art to assay components in a liquid phase may be associated with the vapor phase analysis of the present invention. Large biomolecules such as proteins are not found in VOC off-gas. Assays of antibody and many antigenic larger molecules can add to the assay information obtained using the base system of the present invention. Such information, especially IgM or IgG status can help delineate a patient's historical experience with a disease. Such information can also be helpful in determining the efficacy of immunizations and/or the frequency of recommended booster immunizations. SWNT-based biosensor diagnostic devices in contact with an analyte containing liquid have emerged the current millennium as effective high sensitivity detectors for medical, industrial, environmental, toxicological, quality control, pharmaceutical development, etc., applications. Neutral and ionic compounds in aqueous solutions including, but not limited to: insulin, human chorionic gonadotropin, human growth hormone, prolactin, glucose, fructose, galactose, hormones, neurotransmitters, drugs, amino acids, peptides, proteins, products of micro-organisms—including pathogens and microbiome members, cancer indicative nucleic acids and proteins, etc. have been investigated using such technologies. In a recent review article, electrical, optical, electrochemical, outputs were characterized as sensed signals. Szunerits, S., & Boukherroub, R. (2018). Graphene-based biosensors. Interface focus, 8(3), 20160132. https://doi.org/10.1098/rsfs.2016.0132. Optical properties include light transmission (transparency), light changing (fluorescence), reflecting, and absorbing properties of graphene in various formats. Antigen-antibody complexes are detectable.

Such add-on device could be advantageous when the presence of a large (non-volatile) molecule might be important information. Accordingly, an embodiment of the present invention may incorporate a liquid phase detection component to augment data obtained in the vapor phase.

As an illustrative example of a multi-analysis device, would be one in which two or more types of chips are used. The first type of chip is that of the base device described above to produce the VOC signature. The second type is a chip that analyzes a wet or liquid phase sample. While many alternative form factors may be used, a cartridge (e.g., containing a liquid to off gas the vapors for assay by the first chip) can be configured to incorporate a second type chip that includes sensors for e.g., viral nucleic acid, antigen and or antibodies or other non-volatile compounds of interest. Other configurations may optionally deliver samples to such a liquid phase analysis chip in parallel to delivering vapors to the gas phase sensors. Thus, data from multi-analysis procedures on the same sample can be collated and analyzed together.

Another illustrative example embodies a relatively large protein attached to or in close proximity to the liquid-based NSE(s). Such protein may be a protein with affinity for the molecule in question. When binding said molecule and thus changing its 3-D structure a signal can result in detection of the molecule in question. Such sensor component might be selected to provide immune status, e.g., presence of one or more classes of antibodies or target of the antibody. Enzymes, hormones, hormone receptors, neuro active compounds and receptors are examples of large molecules or proteins that might be assayed in such liquid phase analysis. In some embodiments of the invention the liquid phase and vapor phase may be assaying different components of the same event, such as an antibody active in the lung that might bind SARS-CoV-2 or the liquid phase sensor might sense a VOC that can be assayed in the vapor phase thereby helping to increase confidence in the results. This dual phase multi-analytical system is an advance over existing systems in that it provides, from a single sample, a detailed understanding of an individual's health status.

The ambient vapor phase may be controllably changed in content previous to, during, and post assay operation. The pressure may be changed, e.g., by increasing molecular kinetic energy, changing the amount or mix of a flushing, diluting or supporting gas around the sensing elements, and/or by compressing or reducing total volume. The pressure may be controlled in a predetermined manner or in response to algorithmic or operator input. A preferred mix of gases surrounding the sensor elements contains the sample gas or the sample gas diluted with a known controlled non-reactive gas.

The sensing chip may comprise a single layer or a plurality of layers. A mask may control access of specific gases (VOCs) to a portion or a layer or to a second, third, or subsequent layer. Control may use size, chemical attraction, electrostatic attraction or other filtering means to control access to a portion or the sensor chip and/or to a layer or a part of a layer in a multilayered sensing device.

The chip itself may be heated by contact, resistance, convective, radiance or other means. Gases entering the chamber may be heated prior to introduction with possible effect on sensor temperature. Sensors may be constructed with heating and/or cooling circuitry. Temperatures in the chamber, on a group of sensors or on individual sensors may remain static or may be adjusted during sample, e.g., in a predetermined manner or under algorithmic control.

CONCLUSION

The present invention provides a process and method for assaying volatile organic compounds (VOCs) from a non-invasively obtained biosample. The invention further provides a device that optimizes the capture, decoding, classification, and pattern recognition necessary for identifying a unique VOC signature from VOCs in that biosample. This invention enables signature recognition for presence of a disease at the earliest onset point of that disease, the point where symptoms are starting to rise, but where the person may appear asymptomatic. The invention disclosed herein improves patient experience and outcomes, reduces the number and extent of invasive medical procedures and reduces medical treatment costs through the early identification and detection of disease. In general, this invention increases both survivability and quality of life of patients.

The invention claimed is:

1. An analytical device comprising a detector unit capable of interfacing with an analytical unit,
    said detector unit comprising a plurality of detection surfaces capable of interacting with an ambient vapor phase;
    said detector unit comprising an orifice for introducing a sample to be assayed;
    said detection surface comprising a nano-sensor element (NSE) layer between an input and an output;
    said input in contact with a base power source providing a variable feeder voltage;
    said output in communication with at least one data collector;
    said NSE layer associated with a selection component with selection specificity for one or more compounds of interest;

said selection component when in contact with or in close proximity to a target compound possibly present in said vapor phase selectively altering signal to said output; and a component for collecting said signal from said output.

2. The device of claim 1 wherein said feeder voltage varies between a minimum and a maximum, said minimum >−2 v and said maximum <+4 v.

3. An analytical device comprising a detector unit capable of interfacing with an analytical unit, said detector unit comprising a plurality of detection surfaces capable of interacting with an ambient vapor phase;

said detector unit comprising an orifice for introducing a sample to be assayed;

said detection surface comprising a nano-sensor element (NSE) layer between an input and an output;

said input in contact with a base power source, aid input comprising an input electrode said input electrode having a base or feeder voltage between −10 v and +10 v;

said output in communication with at least one data collector;

said NSE layer associated with a selection component with selection specificity for one or more compounds of interest;

said selection component when in contact with or in close proximity to a target compound possibly present in said vapor phase selectively altering signal to said output; and a component for collecting said signal from said output.

4. An analytical device comprising a detector unit capable of interfacing with an analytical unit, said detector unit comprising a plurality of detection surfaces capable of interacting with an ambient vapor phase;

said detector unit comprising an orifice for introducing a sample to be assayed;

said detection surface comprising a nano-sensor element (NSE) layer between an input and an output;

said input in contact with a base power source;

said output in communication with at least one data collector;

said NSE layer associated with a selection component with selection specificity for one or more compounds of interest;

said selection component when in contact with or in close proximity to a target compound possibly present in said vapor phase selectively altering signal to said output; and a component for collecting said signal from said output;

said analytical device further comprising at least one physical electromagnetic shielding component that shields the sensing chamber from undesired physical effects;

wherein said electromagnetic shielding comprises conductive material.

5. The device of claim 4 wherein said conductive material is selected from the group consisting of: copper, nickel, mu-metal, conductive plastics, conductive paints and conductive inks.

6. An analytical device comprising a detector unit capable of interfacing with an analytical unit, said detector unit comprising a plurality of detection surfaces capable of interacting with an ambient vapor phase;

said plurality of detection surfaces comprising a plurality of nanosensing elements distributed amongst a plurality of groups, at least one of said groups under control of a switch, said switch determining availability of said groups to alter signal to said output and wherein at least two of said groups are controllable to different base voltages;

said detector unit comprising an orifice for introducing a sample to be assayed;

said detection surface comprising a nano-sensor element a SE) layer between an input and an output;

said input in contact with a base power source;

said output in communication with at least one data collector;

said NSE layer associated with a selection component with selection specificity for one or more compounds of interest;

said selection component when in contact with or in close proximity to a target compound possibly present in said vapor phase selectively altering signal to said output; and a component for collecting said signal from said output.

* * * * *